(12) United States Patent
Takii et al.

(10) Patent No.: US 10,602,924 B2
(45) Date of Patent: Mar. 31, 2020

(54) SUBJECTIVE OPTOMETRY APPARATUS

(71) Applicant: NIDEK CO., LTD., Gamagori, Aichi (JP)

(72) Inventors: Michihiro Takii, Nukata (JP); Masaaki Hanebuchi, Nukata (JP); Hisashi Ochi, Nukata (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 18 days.

(21) Appl. No.: 15/942,016

(22) Filed: Mar. 30, 2018

(65) Prior Publication Data
US 2018/0296085 A1 Oct. 18, 2018

(30) Foreign Application Priority Data
Mar. 31, 2017 (JP) ................. 2017-069851

(51) Int. Cl.
*A61B 3/032* (2006.01)
(52) U.S. Cl.
CPC .................. *A61B 3/032* (2013.01)
(58) Field of Classification Search
CPC .................................................... A61B 3/032
See application file for complete search history.

(56) References Cited

U.S. PATENT DOCUMENTS 3,874,774 A  4/1975  Humphrey
6,048,064 A  4/2000  Hosoi et al.

FOREIGN PATENT DOCUMENTS

JP           11-19041 A        1/1999

*Primary Examiner* — Wen Huang
(74) *Attorney, Agent, or Firm* — Sughrue Mion, PLLC

(57) ABSTRACT

A subjective optometry apparatus includes a light projecting optical system which projects a target light flux toward an examinee's eye to project a visual target onto the examinee's eye, a calibration optical system which is disposed in an optical path from the light projecting optical system to the examinee's eye and changes optical characteristics of the target light flux, an optical member which guides the target light flux of which the optical characteristics is changed by the calibration optical system to the examinee's eye, a light deflection section being different from the calibration optical system, which includes light deflection members provided in a left and right pair and a driving section which rotationally drives the light deflection members, and deflects the target light flux by rotating the light deflection members, and a control section which controls the light deflection section based on prism information to deflect the target light flux.

14 Claims, 10 Drawing Sheets

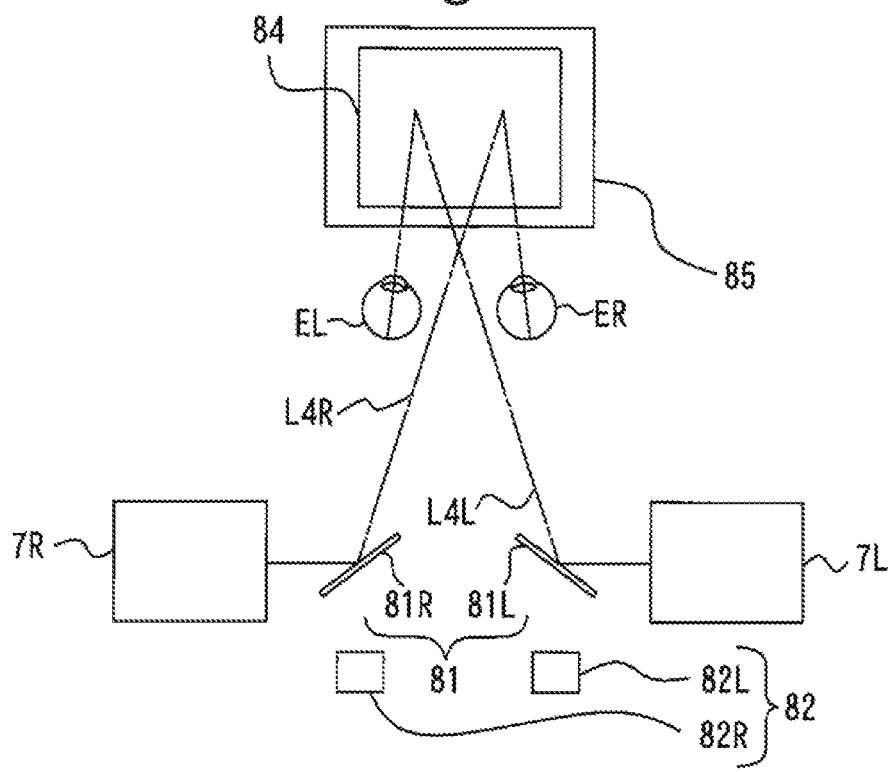
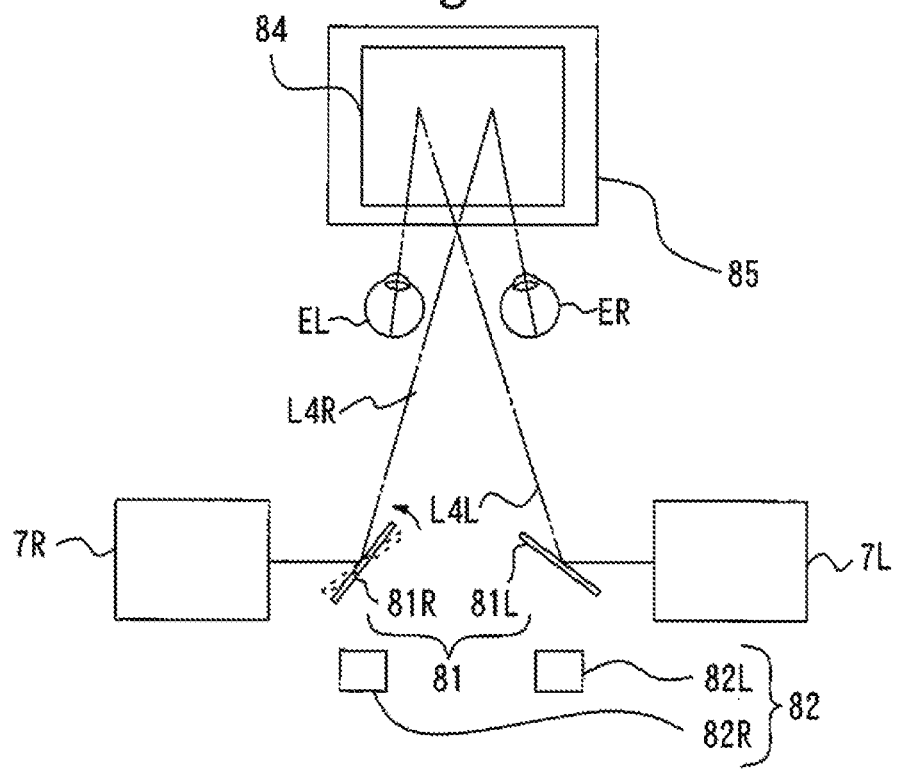

Left eye    Right eye

Left eye    Right eye

SUBJECTIVE OPTOMETRY APPARATUS

CROSS-REFERENCE TO RELATED APPLICATION

This application claims priority from Japanese Patent Application No. 2017-069851 filed on Mar. 31, 2017, the entire subject-matter of which is incorporated herein by reference.

TECHNICAL FIELD

The present disclosure relates to a subjective optometry apparatus that subjectively measures optical characteristics of an examinee's eye.

BACKGROUND

In recent years, for example, there has been known a subjective optometry apparatus which is configured such that calibration optical systems capable of calibrating refractivity are individually disposed in front of eyes of an examinee, and is configured to project an examination visual target onto a fundus of the examinee's eye through the calibration optical system. An examiner receives the response of the examinee and adjusts the calibration optical systems until the visual target is appropriately seen by the examinee to thereby obtain a calibration value, and measures a refractive power of the examinee's eye based on the calibration value. In addition, there has been known a subjective optometry apparatus which is configured to form an image of an examination visual target through a calibration optical system in front of the eyes of an examinee, and is configured to measure a refractive power of the examinee's eye without disposing the calibration optical system in front of the eyes (for example, refer to U.S. Pat. No. 3,874,774).

In the subjective optometry apparatus described above, it is possible to examine an oblique position or visual functions, such as a divergence power or a convergence power, by changing the prism power applied to the examinee's eye. A rotary prism in the calibration optical system is used for applying the prism power to the examinee's eye (for example, refer to JP-A-H11-19041).

However, in the subjective optometry apparatus described above, in a case of examining the visual function by changing the prism power applied to the examinee's eye, it is necessary to use a dedicated optical member (for example, a rotary prism) provided in the calibration optical system and a configuration for controlling the optical member. Therefore, a space is required since the configuration of the calibration optical system becomes large, and complicated control is required from the relationship with other members in the calibration optical system.

SUMMARY

An object of the present disclosure is to provide a subjective optometry apparatus which does not require complicated control and can easily examine a visual function with a simple configuration.

In order to solve the above-described problem, the invention includes the following configurations.

(1) A subjective optometry apparatus that subjectively measures optical characteristics of an examinee's eye, including:

a light projecting optical system that includes a right eye light projecting optical system and a left eye light projecting optical system which are provided in a left and right pair, and projects a target light flux toward the examinee's eye to project a visual target onto the examinee's eye;

a calibration optical system that includes a right eye calibration optical system and a kit eye calibration optical system which are provided in a left and right pair, is disposed in an optical path from the light projecting optical system to the examinee's eye, and changes optical characteristics of the target light flux;

an optical member that guides the target light flux of which the optical characteristics is changed by the calibration optical system to the examinee's eye, a light deflection section that is a member different from the calibration optical system includes light deflection members provided in a left and right pair respectively and a driving section configured to rotationally drive the light deflection members, and deflects the target light flux by rotating the light deflection members;

a setting section that sets prism information; and a control section that controls the light deflection section based on the prism information set by the setting section to deflect the target light flux.

(2) The subjective optometry apparatus according to the above-described (1), in which each of the light deflection members is disposed at a position conjugated with a pupil of the examinee's eye in the light projecting optical system.

(3) The subjective optometry apparatus according to the above-described (1), in which the light deflection section deflects the target light flux in two dimensions.

The subjective optometry apparatus according to the above-described (1), further including:

a deviation detection section that detects a deviation of the target light flux with respect to the examinee's eye, in which the control section controls the light deflection section based on a detection result detected by the deviation detection section to deflect the target light flux.

(5) The subjective optometry apparatus according to the above-described (1), further including:

a pupillary distance selling section that sets a pupillary distance, in which the control section controls the light deflection section based on the pupillary distance to deflect the target light flux.

(6) The subjective optometry apparatus according to the above-described (1), further including:

a convergence amount setting section that sets a convergence amount of the light projecting optical system, in which the control section controls the light deflection section based on the convergence amount to deflect the target light flux.

(7) The subjective optometry apparatus according to the above-described (1).

in which the light projecting optical system includes a light source configured to project the target light flux toward the examinee's eye, and the light deflection members are disposed in an optical path between the optical member and the light source.

(8) A subjective optometry apparatus that subjectively measures optical characteristics of an examinee's eye, including:

a light projecting optical system that includes a right eye light projecting optical system and a left eye light projecting optical system which are provided in a left and right pair, and emits a target light flux toward the examinee's eye by displaying a visual target on a display to project the visual target onto the examinee's eye:

a calibration optical system that includes a right eye calibration optical system and a left eye calibration optical system which are provided in a left and right pair, is disposed in an optical path from the light projecting optical system to the examinee's eye, and changes optical characteristics of the target light flux;

an optical member that guides the target light flux of which the optical characteristics is changed by the calibration optical system to the eye;

a setting section that sets prism information; and a control section that changes a position of the visual target displayed on the display based on the prism information set by the setting section.

BRIEF DESCRIPTION OF DRAWINGS

FIGS. 9A and 9B are views for describing application of a prism using a deflection mirror.

DETAILED DESCRIPTION

Figure 1:
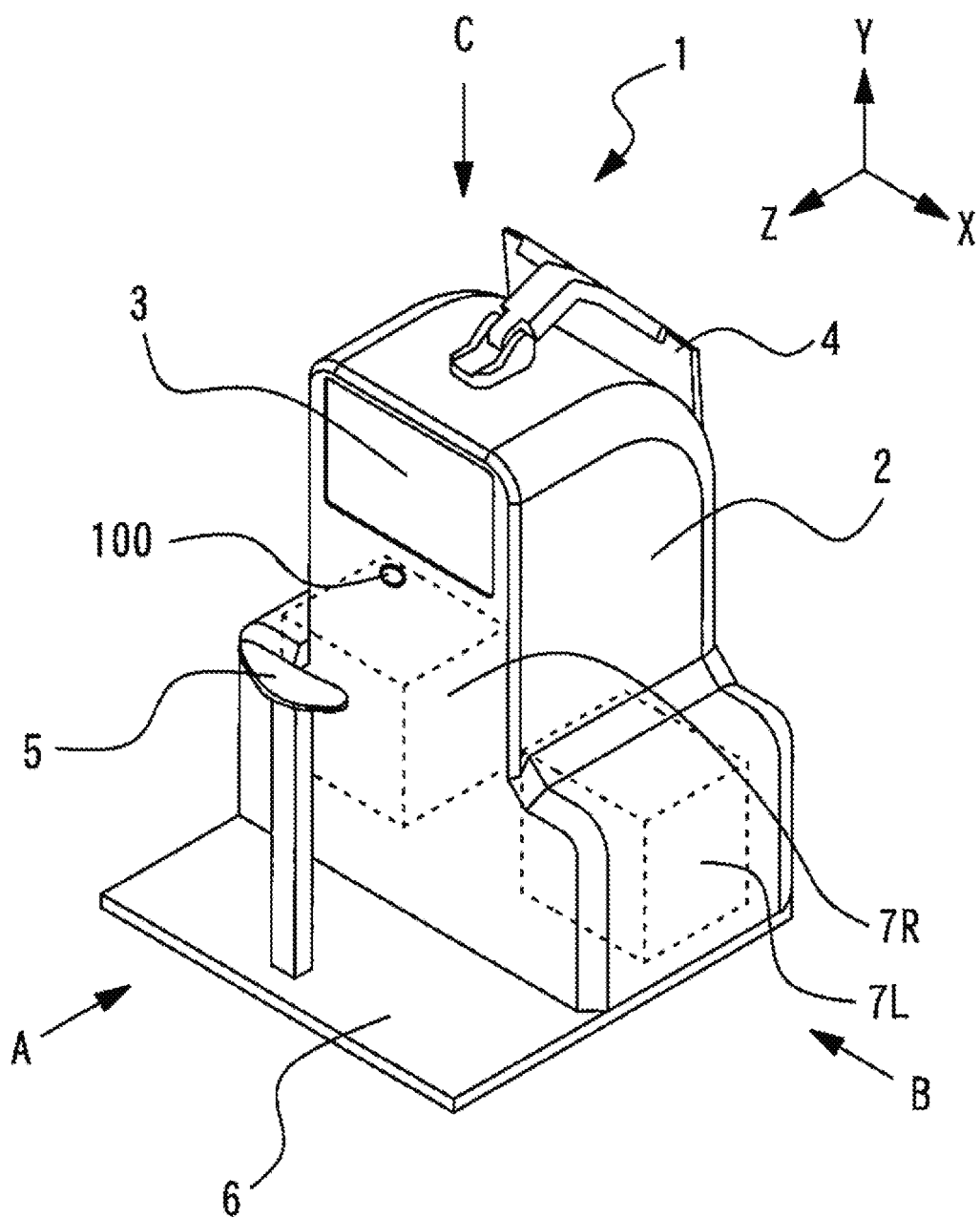
FIG. 1 is an exterior view of a subjective optometry apparatus.

Hereinafter, one of typical embodiments will be described with reference to the accompanying drawings. FIGS. 1 to 10C are views illustrating; a subjective optometry apparatus according to the embodiment. In addition, in the following description, a subjective optometry apparatus will be described as an example. Meanwhile, items classified as the following sign "< >" may be used independently of or in relation to each other.

Further, in the following description, a description will be given on the assumption that a depth direction (a front-back direction of an examinee when the examinee is measured) of the subjective optometry apparatus is a Z direction, a horizontal direction on a plane which is perpendicular (a left-right direction of the examinee when the examinee is measured) to the depth direction is an X direction, and a vertical direction (an up-down direction of the examinee when the examinee is measured) is a Y direction. Meanwhile, R and L attached to reference numerals are assumed to be signs for the right eye and the left eye, respectively.

<Outline>

For example, the subjective optometry apparatus (for example, a subjective optometry apparatus 1) in the present embodiment subjectively measures optical characteristics of a an examinee's eye. For example, the subjective optometry apparatus may include a light projecting optical system (for example, a light projecting optical system 30). For example, the light projecting optical system projects a target light flux toward the examinee's eye to project a visual target onto the examinee's eye. In addition, for example, the subjective optometry apparatus may include a calibration optical system (for example, a calibration optical system 60 and a subjective measurement optical system 25. For example, the can bra lion optical system is disposed in an optical path from the light projecting optical system to the examinee's eye and changes the optical characteristics of the target light flux. Also, for example, the subjective optometry apparatus may include an optical member (for example, a concave surface mirror 85 is that guides the target light flux corrected by the calibration optical system to the examinee's eye.

Examples of the optical characteristics of the examinee's eye which is subjectively measured include an eye refractive power (for example, a spherical power, an astigmatic power, or an astigmatic axis angle), a contrast sensitivity, a binocular visual function (for example, an amount of oblique position, a divergence power, or a convergence power), and the like.

For example, the subjective optometry apparatus may include a light deflection section (for example, deflection mirrors 81 and driving sections 82) which makes it possible to deflect the target light flux. For example, the light deflection section may be a member different from the calibration optical system and may include light deflection members (for example, the deflection mirrors 81) provided in a left and right pair respectively. For example, the light deflection section may have a driving section (for example, the driving sections 82) for rotationally driving the light deflection member. For example, the light deflection section may be capable of deflecting the target light flux by rotationally driving the light defection member.

For example, the subjective optometry apparatus may include a setting section (for example, a control section 70) which sets prism information relating to deflection of a line of sight of an examinee. For example, the subjective optometry apparatus may include the control section (for example, the control section 70) which controls the light deflection section based on the prism information set by the setting section and deflects the target light flux. For example, the prism information may be at least one of a prism power indicating the deflection amount of the line of sight of the examinee, a base direction of the prism indicating a deflection direction of the line of sight of the examinee, and the like. For example, with such a configuration, complicated control is not required and it is possible to easily examine a visual function with a simple configuration.

<Light Projecting Optical System>

For example, in the present embodiment, the light projecting optical system may include a right eye light projecting optical system and a left eye light projecting optical system which are provided in a left and right pair. For example, the right eye light projecting optical system and the left eye light projecting optical system may be configured such that members configuring the right eye light projecting optical system and members configuring the left eye light projecting optical system are the same members. In addition, for example, the right eye light projecting optical system and the left eye light projecting optical system may be configured such that at least some of the members configuring the right eye light projecting optical system and the members configuring the left eye light projecting optical system are members different from each other. For example, the right eye light projecting optical system and the left eye light projecting optical system may be configured such that at least some of the members configuring the right eye light projecting optical system and the members configuring the left eye light projecting optical system are used in common. In addition, for example, the right eye light projecting optical system and the left eye light projecting optical system may be configured such that the members configuring the right eye light projecting optical system and the members configuring the left eye light projecting optical system are separately provided.

For example, the light projecting optical system includes a light source that projects the target light flux. In addition, for example, the light projecting optical system include at least one or more optical members that guide the target light flux projected front the light source projecting the target light flux toward the examinee's eye.

For example, a configuration may also be adopted in which a display (for example, a display 31) is used as the light source that projects the target light flux. For example, a liquid crystal display (LCD), an organic electroluminescence (EL), or the like is used as the display. For example, an examination visual target such as a Landolt ring visual target is displayed on the display.

For example, a light source and a digital micromirror device (DMD) may be used as the light source that projects the target light flux, in general, the DMD has high reflectivity and luminance. Therefore, it is possible to maintain the amount of light of the target light flux as compared to a case where a liquid crystal display using polarization is used.

For example, the light source projecting the target light flux may be configured to include a visual target presentation visible light source and a visual target plate. In this case, for example, the visual target plate is a rotatable disc plate, and includes a plurality of visual targets. The plurality of visual targets include, for example, a visual target for examination of visual acuity which is used during subjective measurement, and the like. For example, regarding the visual target for examination of visual acuity, a visual target (visual acuity value 0.1, 0.3, . . . , 1.5) is provided for each visual acuity value. For example, the visual target plate is rotated by a motor or the like, and the visual targets are disposed in a switching manner in an optical path through which the target light flux is guided to the examinee's eye. Naturally, a light source other than the light source having the above-described configuration may be used as the light source projecting the target light flux.

<Calibration Optical System>

For example, in the present embodiment, the calibration optical system includes a right eye calibration optical system and a left eye calibration optical system which are provided in a left and right pair. For example, the right eye calibration optical system avid the left eye calibration optical system may be configured such that members configuring the right eye calibration optical system and members configuring the left eye calibration optical system are the same members. In addition, for example, the right eye calibration optical system and the left eye calibration optical system may be configured such that at least some of the members configuring the right eye calibration optical system and the members configuring the left eye calibration optical system are members different from each other. For example, the right, eye calibration optical system and the left eye calibration optical system may be configured such that at least some of the members configuring the right eye calibration optical system and members configuring the left eye calibration optical system are used in common. In addition, for example, the right eye calibration optical system and the left eye calibration optical system may be configured such that the members configuring the right eye calibration optical system and the members configuring the left eye calibration optical system are separately provided.

For example, the calibration optical system may be configured to change optical characteristics (for example, at least any one of a spherical power, a cylindrical power, a cylindrical axis, polarization characteristics, and the amount of aberration) of the target light flux. For example, as a configuration in which the optical characteristics of the target light flux is changed, a configuration in which an optical element is controlled may be adopted. For example, as the optical element, a configuration may also be adopted in which at least any one of a spherical lens, a cylindrical lens, a cross cylinder lens, a wave front modulation element, and the like is used. Naturally, for example, as the optical element, an optical element different from the optical element having the above-described configuration may be used.

For example, the calibration optical system may be configured such that a spherical power of the examinee's eye is calibrated by a presentation position (presenting distance) of the visual target with respect to the eyes of the examinee is optically changed. In this case, for example, as a configuration in which the presentation position (presenting distance) of the visual target is optically changed, a commutation may also be adopted in which a light source (for example, a display) is moved in an optical axis direction. In addition, in this case, for example, a configuration may also be adopted in which the optical element (for example, a spherical lens) which is disposed in the optical path is moved in the optical axis direction. Naturally, the calibration optical system may have a configuration constituted by a configuration in which the optical element is controlled and a configuration in which the optical element disposed in the optical path is moved in the optical axis direction.

For example, the calibration optical system may be configured to change the optical characteristics of the target light, flux by disposing, the optical element between the optical member (optical member which guides the target light flux calibrated by the calibration optical system to the examinee's eye) for guiding the target light flux toward the examinee's eye from the light projecting optical system and the light source that projects the target light flux in the light protecting optical system and by controlling the optical element. In other words, the calibration optical system may have a configuration of a phantom lens refractometer (phantom calibration optical system). In this case, for example, the target light flux calibrated by the calibration optical system is guided to the examinee's eye through the optical member, <Optical Member>

For example, the optical member which guides the target light flux calibrated by the calibration optical system to the examinee's eye may be an optical member which guides an image of the target light flux optically to the examinee's eye so as to have a predetermined examination distance. For example, the concave surface mirror may be used for the optical member. For example, by using the concave surface mirror, it becomes possible to optically present the visual target to a predetermined examination distance in the subjective examination means and when presenting the visual target to the predetermined examination distance, it is unnecessary to dispose a member or the like to have an actual distance. According to this, since an extra member and space are not required, it is possible to reduce the size of the apparatus. Naturally, for example, the optical member is not limited to the concave surface mirror. For example, the optical member may have any configuration as long as the optical member guides the image of the target light flux optically to the examinee's eye so as to have the predetermined examination distance. In this case, for example a lens or the like may be used as the optical member.

<Light Deflection Section>

For example, the light deflection member in the light deflection section may be a member which reflects the target light flux projected from the light projecting optical system and guides the target light flux, to the examinee's eye. For example, as the light deflection member, at least one of the mirror, the lens, the prism, and the like may be used. For example, the light deflection members provided in a left and right pair respectively may be configured with at least one or more members. For example, the light deflection members provided in a left and right pair respectively may be configured with two members respectively (for example, two light deflection members in the optical path for the right eye).

For example, the driving section for rotationally driving the light deflection member may be a motor or the like. For example, in order to rotationally drive the light deflection members provided in a left and right pair respectively, a configuration may be adopted in which the driving sections are provided respectively for each of the light deflection members. Further, for example, in order to rotationally drive the light deflection members provided, in a left and right pair respectively, a configuration may also be adopted in which the driving section is used in common by the light deflection members provided in a left and right pair respectively.

For example, the light deflection member may be disposed at a position conjugated with the pupil of the examinee's eye in the light projecting optical system. In addition, as the configuration disposed in the position conjugated with the pupil, a configuration disposed substantially at the position conjugated with the pupil is included. According to this, it is possible to examine the visual function for example, without increasing a driving range of the light deflection member. In other words, the light deflection section can be made smaller, and the size of the apparatus can be reduced. Naturally, for example, the light deflection member may be configured to be disposed in the optical path of the light projecting optical system.

For example, the light deflection member may be disposed in the optical path between the optical member and the light source of the light projecting optical system. In addition, for example, the light deflection member may be disposed in the optical path between the optical member and the light source.

For example, the light deflection section may be configured to be capable of being rotationally driven around a rotation axis in which the light deflection member extends in the vertical direction (Y direction). For example, as the light deflection member is rotated around the rotation axis that extends in the vertical direction (up-down direction), the light deflection member is tilted in the horizontal direction (X direction) with respect to the optical axis direction of the light projecting optical system. In other words, for example, the light deflection section may be configured to be capable of changing the rotation angle of the light deflection member in the horizontal direction (left-right direction) with respect to the optical axis of the light projecting optical system. With such a configuration, the light deflection section can deflect a projection position of the target light flux with respect to the examinee's eye in the left-right direction. In addition, for example, the light deflection section may be configured to be capable of rotationally driving the light deflection member around the rotation axis that extends in the up-down, direction from the center of the light deflection member. In addition, for example, the light deflection section may be configured to be capable of rotationally driving the light deflection member around the rotation axis that extends in the up-down direction from the position different from the center of the light reflection member.

For example, the light deflection section may be configured to be capable of being rotationally driven around the reunion axis in which the light deflection member extends in the horizontal direction (X direction). For example, as the light deflection member is rotated around the rotation axis that extends in the horizontal direction (left-right direction), the light deflection member is tilted in the vertical direction (Y direction) with respect to the optical axis direction of the light projecting optical system. In other words, for example, the light deflection section may be configured to be capable of changing the rotation angle of the light deflection member in the vertical direction (up-down direction) with respect to the optical axis of the light projecting optical system. With such a configuration, the light deflection section can deflect the projection position of the target light flux with respect to the examinee's eye in the up-down direction. In addition, for example, the light deflection section may be configured to be capable of rotationally driving the light deflection member around the rotation axis that extends in the left-right direction from the center of the light deflection member. In addition, for example, the light deflection section may be configured to be capable of rotationally driving the light deflection member around the rotation axis that extends in the left-right direction from the position different from the center of the light deflection member.

For example, the light deflection section may be configured to be capable of two-dimensionally deflecting the target light flux. In this case, for example, the light deflection members may be configured to be rotationally driven around the rotation axis that extends in the left-right direction and the rotation axis that extends in the up-down direction by driving the driving section respectively. In other words, for example, the light deflection section may be configured to be capable of changing the rotation angle of the light deflection member in the X and Y directions with respect to the optical axis of the light projecting optical system. With such a configuration, the light deflection section can deflect the projection position of the target light flux with respect to the examinee's eye in various directions, such as the up-down and left-right directions. Therefore, it is possible to easily examine mote visual functions with a simple configuration. In addition, as a configuration in which the target light flux can be two-dimensionally deflected, the driving section which rotates the light deflection member in the X and Y directions may be a common driving section. In this case, for example, a configuration for being two-dimensionally rotated around any position on the light deflection member may also be adopted.

<Setting Section>

For example, in the setting section which sets the prism information, a configuration may be adopted in which the examiner sets the input prism information by operating the operation section. Further, for example, a configuration may also be adopted in which the setting section which sets the prism information automatically sets predetermined prism information. In this case, for example, a configuration may also be adopted in which the preset prism information is automatically set. In this case, for example, the setting section may be configured to receive prism information acquired by another apparatus by the reception means and set the received prism information. In this case, for example, a configuration may be adopted in which the setting section analyzes an anterior ocular segment image captured by the observation optical system (for example, an observation optical system 50) provided in the subjective optometry apparatus and sets the prism information based on a detection result obtained by detecting the position of the examinee's eye (for example, the position of the pupil of the examinee's eye and the cornea apex position).

<Control Section>

For example, the control section may control the light deflection section based on the prism information set by the setting section to deflect the target light flux. For example, any prism can be applied by the control section controlling the light deflection section based on the prism information. For example, the control section can apply any prism to the examinee's eye by driving the driving section and controlling the rotational driving of the light deflection member.

For example, the control section applies any prism power to the examinee's eye by driving the driving section and controlling the angle oft be light deflection member. For example, the control section can apply (set) the base direction of the prism by controlling the rotation direction.

For example, in a case where the prism power is applied by the light deflection section, a configuration for controlling the rotational driving of the light deflection member such that the angle of the light deflection member becomes a predetermined angle may be adopted. In addition, for example, in a case where the prism power is applied by the light deflection section, a configuration for controlling the angle of the light deflection member to be a predetermined angle by rotationally driving the light deflection member only by a predetermined rotation amount may be adopted. In other words, the rotational driving control of the light deflection member may be controlled such that the light deflection member has a predetermined angle. For example, in a case of applying the prism, at least one of the light deflection members provided in a left and right pair may be configured to be rotationally driven.

For example, in a case of applying the prism power by the light deflection section, a table may be created in which the angle of the light deflection member is set for each prism power in advance, and the created table may be stored in a memory (for example, a memory 72). In this case, for example, the control section may call the angle of the light deflection member that corresponds to the prism power from the memory and control the rotational driving of the light deflection member so as to have the called angle. In addition, for example, regarding the angle of the light deflection member, an arithmetic expression for calculating the angle of the light deflection member for each prism power may be stored in the memory, and the angle of the light deflection member may be obtained using the arithmetic expression.

For example, in a case of setting the base direction of the prism by the light deflection section, the rotation direction of light deflection member may be stored in advance in the memory (for example, the memory 72) for each base direction. In this case, for example, the control section may call the rotation direction of the light deflection member that corresponds to the base direction of the prism from the memory and control the rotational driving of the light deflection member such that the light deflection member rotates in the called rotation direction.

<Deviation Detection Section>

For example, the subjective optometry apparatus may include a deviation detection section (for example, the control section 70) to detect the deviation of the target light flux with respect so the examinee's eye. In this case, for example, the control section may control the light deflection section based on the detection result obtained by the detection of the deviation detection section to deflect the target light flux. In other words, for example, the light deflection section serves both as the configuration for applying the prism to the examinee's eye and the configuration for correcting the deviation of the examinee's eye. For example, in a case of correcting the deviation, at least one of the light deflection members provided in a left and right pair may be configured to be rotationally driven. For example, with such a configuration, in a case of examining the visual function by changing the prism applied to the examinee's eye, it is possible to easily examine the visual function with a simpler configuration without providing an optical member dedicated to the calibration optical system. Further, for example, it is possible to perform a visual function examination and a deviation correction performed with the applied prism with a simpler configuration. Further, for example, it is possible to apply the prism, to perform the deviation correction, and to smoothly examine the visual function.

In addition, in a case of correcting the deviation, a configuration may be adopted in which the position of at least one light deflection member of the light deflection members provided in a left and right pair moves. In this case, for example, the control section may drive the driving section that moves the position of the light deflection member, control the movement of the position of at least one light deflection member of the light deflection members provided in a left and right pair, and control the rotational driving of at least one light deflection member of the light deflection members provided in a left and right pair.

For example, the deviation detection section which uses an alignment index light projecting optical system (for example, a first index projection optical system 45 and a second index projection optical system 46) which projects alignment light to the examinee's eye and forms an alignment index on the periphery of the cornea, can be mentioned. In this case, for example, the deviation detection section may be configured to detect a relative position of the examinee's eye and the projection position (optical axis of the light projecting optical system) of the target light flux by detecting the alignment state bused on the alignment index captured by an anterior ocular segment observation optical system (for example, the observation optical system 50). Further, for example, the deviation detection section may be configured to detect the position of the pupil from the anterior ocular segment front image captured by the anterior ocular segment observation optical system and detect the relative position of the detected position of the pupil and the projection position (optical axis of the light projecting optical system) of the target light flux.

For example, the deviation detection section may be configured to detect the deviation in the left-right direction (X direction) between the examinee's eye and the optical axis of the light projecting optical system. In this case, for example, the control section rotationally drives the light deflection member in the left-right direction based on the deviation amount in the left-right direction. Accordingly, the control section may deflect the target light flux in the left-right direction and correct the deviation in the left-right direction. In addition, for example, the deviation detection section may be configured to detect the deviation in the up-down direction (Y direction) between the examinee's eye and the optical axis of the light projecting optical system. In this case, for example, the control section rotationally drives the light deflection member in the up-down direction based on the deviation amount in the up-down direction. Accordingly, the control section may deflect the target light flux in the up-down direction and correct the deviation in the up-down direction.

For example, the deviation detection section may be configured to detect the deviation in the front-back direction (Z directions of the examinee's eye and the subjective optometry apparatus. In this case, for example, the control section rotationally drives the light deflection member in the left-right and up-down directions based on the deviation amount in the front-back direction. Accordingly, the control section may deflect the target light flux in the left-right and up-down directions and correct the deviation in the front-back direction. In addition, for example, the deviation detection section may be configured to detect the deviation in the front-back direction (Z direction) of the examinee's eye and the subjective optometry apparatus. In this case, for example, the control section rotationally drives the light deflection member in the up-down and left-right direction based on the deviation amount in the front-back direction. Accordingly, the control section may deflect the target light flux in the up-down and left-right direction and correct the deviation in the front-back direction.

For example, the deviation correction and the application of the prism power may be performed separately at different timings. In addition, for example, the deviation correction and the application of the prism power may be performed at the same timing. Here, the term "the same" includes substantially the same.

For example, in a case of performing the deviation correction and the application of the prism power by the light deflection section, a table may be created in which the angle of the light deflection member is set for each prism power and the deviation amount in advance, and the created table may be stored in the memory. In this case, for example, the control section may call the angle of the light deflection member that corresponds to the prism power and the deviation amount from the memory and control the rotational driving of the light deflection member so as to have the called angle. In addition, for example, regarding the angle of the light deflection member, an arithmetic expression for calculating the angle of the light deflection member for each prism power and the deviation amount may be stored in the memory, and the angle of the light deflection member may be obtained using the arithmetic expression.

For example, in a case of selling the deviation correction and the base direction of the prism by the light deflection section, the rotation direction of light deflection member may be stored in advance in the memory (for example, the memory 72) for each deviation direction and the base direction. In this case, for example, the control section may call the rotation direction of the light deflection member that corresponds to the deviation direction and the base direction from the memory and control the rotational driving of the light deflection member such that the light deflection member rotates in the called rotation direction. In addition, for example, regarding the rotation direction of the light deflection member, an arithmetic expression for calculating the rotation direction of the light deflection member based on the deviation direction and the base direction may be stored, in the memory, and the rotation direction of the light deflection member may be obtained using the arithmetic expression.

<Setting of Pupillary Distance>

For example, the subjective optometry apparatus may include a pupillary distance setting section (for example, the control section 70) for setting the pupillary distance. In this case, for example, the control section may control the light deflection section based on the pupillary distance to deflect the target light flux. In other words, for example, the light deflection section serves both as the configuration for applying the prism to the examinee's eye and the configuration for adjusting the pupillary distance. For example, in a case of adjusting the pupillary distance, at least one of the light deflection members provided in a left and right pair may be configured to be rotationally driven. For example, with such a configuration, in a case of examining the visual function by changing the prism applied to the examinee's eye, it is possible to easily examine the visual function with a simpler configuration without providing an optical member dedicated to the calibration optical system. Further, for example, it is possible to perform the visual function examination and the adjustment of the pupillary distance which are performed with the applied prism with a simpler configuration. Further, for example, it is possible to apply the prism, to perform the adjustment of the pupillary distance, and to smoothly examine the visual function.

In addition, in a case of adjusting the pupillary distance, a configuration may be adopted in which the position of at least one light deflection member of the light deflection members provided in a left and right pair moves, hi this case, for example, the control section may drive the driving section (for example, driving sections 83) that moves the position of the light deflection member, control the movement of the position of at least one light deflection member of the light deflection members provided in a left and right pair, and control the rotational driving of at least one light deflection member of the light deflection members provided in a left and right pair. As an example, for example, in a case of adjusting the pupillary distance, the control section may move the position of the light deflection member in the left-right direction and change the angle of the light deflection member based on the pupillary distance.

For example, in the pupillary distance setting section which sets the pupillary distance, a configuration may be adopted in which the examiner sets the input pupillary distance by operating the operation section. Further, for example, a configuration may also be adopted in which the pupillary distance setting section which sets the pupillary distance automatically sets a predetermined pupillary distance. In this case, for example, a configuration may also be adopted in which the preset pupillary distance is automatically set. In this case, for example, the pupillary distance setting section may be configured to receive the pupillary distance acquired by another apparatus by the reception means and set the received pupillary distance.

For example, the adjustment of the pupillary distance and the application of the prism power may be performed separately at different timings. In addition, for example, the adjustment of the pupillary distance and the application of the prism power may be performed at the same timing. Here, the term "the same" includes substantially the same.

For example, in a case of performing the adjustment of the pupillary distance and the application of the prism power by the light deflection section, a table may be created in which the angle of the light deflection member is set for each prism power and the pupillary distance in advance, and the created table may be stored in the memory, in this case, for example, the control section may call the angle of the light deflection member that corresponds to the prism power and the pupillary distance from the memory and control the rotational driving of the light deflection member so as to have the called angle. In addition, for example, regarding the angle of the light deflection member, an arithmetic expression for calculating the angle of the light deflection member for each prism power and the pupillary distance may be stored in the memory, and the angle of the light deflection member may be obtained using the arithmetic expression.

For example, in a case of adjusting the pupillary distance and setting the base direction of the prism by the light deflection section, the rotation direction of the light deflection member may be stored in advance in the memory for each pupillary distance and base direction. In this case, for example, the control section may call the rotation direction of the light deflection member that corresponds to the pupillary distance and the base direction from the memory and control the rotational driving of the light deflection member such that the light deflection member rotates in the called rotation direction. In addition, for example, regarding the rotation direction of the light deflection member, an arithmetic expression for calculating the rotation direction of the light deflection member based on the pupillary distance and the base direction may be stored in the memory, and the rotation direction of the light deflection member may be obtained using the arithmetic expression.

<Setting of Convergence Amount>

For example, the subjective optometry apparatus may include a convergence amount setting section (for example, the control section 70) for setting the convergence amount of the light projecting optical system. In this case, for example, the control section may control the light deflection section based on the convergence amount to deflect the target light flux. In other words, for example, the light deflection section serves both as the configuration for applying the prism to the examinee's eye and the configuration for adjusting the convergence amount. For example, with such a configuration, in a case of examining the visual function by changing the prism applied to the examinee's eye, it is possible to easily examine the visual function with a simpler configuration without providing an optical member dedicated to the calibration optical system. Further, for example, it is possible so perform the visual function examination and the adjustment of the convergence amount of the light projecting optical system which are performed with the applied prism with a simpler configuration. In addition, for example, it is possible to apply the prism, to perform the adjustment of the convergence amount, and to smoothly examine the visual function.

In addition, in a case of adjusting the convergence amount, a configuration may be adopted in which the position of at least one light deflection member of the light deflection members provided in a left and right pair moves. In this case, for example, the control section may drive the driving section that moves the position of the light deflection member, control the movement of the position of at least one light deflection member of the light deflection members provided in a left and right pair, and control the rotational driving of at least one light deflection member of the light deflection members provided in a left and right pair.

For example, in the convergence amount setting section which sets the convergence amount of the light projecting optical system, a configuration may be adopted in which the examiner sets the input convergence amount by operating the operation section. Further, for example, a configuration may also be adopted in which the convergence amount setting section which sets the convergence amount of the light projecting optical system automatically sets a predetermined convergence amount. In this case, for example, a configuration may also be adopted in which the preset convergence amount is automatically set. In this case, for example, the convergence amount setting section may be configured to receive the convergence amount acquired by another apparatus by the reception means and set the received convergence amount.

For example, in a case of adjusting the convergence amount by the light deflection section, the convergence amount cars be adjusted by setting the angle of the light deflection member to a predetermined angle so as to have the set convergence amount. For example, in a case where the convergence amount is adjusted by the light deflection section, a configuration for controlling the rotational driving of the light deflection member such that the angle of the light deflection member becomes a predetermined angle may be adopted. In addition, for example, in a case where the convergence amount is adjusted by the light deflection section, a configuration for controlling the angle of the light deflection member to be a predetermined angle by rotationally driving the light deflection member only by a predetermined rotation amount may be adopted. In other words, the rotational driving control of the light deflection member may be controlled such that the light deflection member has a predetermined angle. For example, in a case of adjusting the convergence amount, at least one of the light deflection members provided in a left and right pair may be configured to be rotationally driven.

For example, the adjustment of the convergence amount and the application of the prism power may be performed separately at different timings. In addition, for example, the adjustment of the convergence amount and the application of the prism power may be performed at the same timing. Here, the term "the same" includes substantially the same.

For example, in a cast of performing the adjustment of the convergence amount and the application of the prism power by the light deflection section, a table may be created in which the angle of the light deflection member is set for each prism power and the convergence amount in advance, and the created table may be stored in the memory. In this case, for example, the control section may call the angle of the light deflection member that corresponds to the prism power and the convergence amount from the memory and control the rotational driving of the light deflection member so as to have the called angle. In addition, for example, regarding the angle of the light deflection member, an arithmetic expression for calculating the angle of the light deflection member for each prism power and the convergence amount may be stored in the memory, and the angle of the light deflection member may be obtained using the arithmetic expression.

For example, in a case of adjusting the convergence amount and setting the base direction of the prism by the light deflection section, the rotation direction of the light reflection member may be stored in advance in the memory for each convergence amount and base direction. In this case, for example, the control section may call the rotation direction of the light deflection member that corresponds to the convergence amount and the base direction from the memory and control the rotational driving of the light deflection member such that the light deflection member rotates in the called rotation direction. In addition, for example, regarding the rotation direction of the light deflection member, an arithmetic expression for calculating the rotation direction of the light deflection member based on the convergence amount and the base direction may be stored in the memory, and the rotation direction of the light deflection member may be obtained using the arithmetic expression.

In addition, in a case of adjusting the convergence amount, the alignment state may be adjusted.

Modified Example

In addition, for example, the light deflection section may be configured to be capable of performing at least one of the deviation correction, the adjustment of the pupillary distance, and the adjustment of the convergence amount, and the application of the prism. For example, the configuration may be adopted in which it is possible to perform the deviation correction, the adjustment of the pupillary distance, the adjustment of the convergence amount, and the application of the prism using the light deflection section. In this case, for example, the control section may control the rotation direction and the angle of the light deflection member based on the deviation correction, the adjustment of the pupillary distance, the adjustment of the convergence amount, and the prism information.

In addition, in the present embodiment, a configuration may be adopted in which at least two or more of the control section, the setting section, the deviation detection section, the pupillary distance setting section, and the convergence amount setting section may be used in common. Further, for example, a configuration may be adopted in which the control section, the setting section, the deviation detection section, the pupillary distance setting section, and the convergence amount setting section may be separately provided. Naturally, each of the above-described control sections may be configured with a plurality of control sections.

In addition, in the present embodiment, a configuration in which the prism is applied to the examinee's eye using the light deflection section has been described as an example, but the invention is not limited thereto. For example, a configuration may be adopted in which the prism is applied to the examinee's eye by changing the position of the visual target displayed on the display. In this case, for example, the subjective optometry apparatus may include: the light projecting optical system which includes the right eye light projecting optical system and the left eye light projecting optical system which are provided in a left and right pair and emits the target light flux toward the examinee's eye to project the visual target onto the examinee's eye by displaying the visual target on the display; and the calibration optical system which includes the right eye calibration optical system and the left eye calibration optical system which are provided in a left and right pair, is disposed in be optical path of the light projecting optical system, and changes the optical characteristics of the target light flux, and subjectively measure the optical characteristics of the examinee's eye. Further, for example, the setting section which sets the prism information and the control section which changes the position of the visual target displayed on the display based on the prism information set by the setting section may be provided. For example, with such a configuration, complicated control is not required and it is possible to easily examine a visual function with a simple configuration.

For example, a configuration may be adopted in which the displays are provided in each of the light projecting optical systems provided in a left and right pair. In this case, for example, by controlling each of the left and right displays, it is possible to apply the prism, to adjust the convergence amount, and the like. In addition, a configuration may be adopted in which the displays are used in common in the light projecting optical systems provided in a left and right pair.

For example, the control section can apply any prism power to the examinee's eye by changing the movement amount (the shift amount of the display position of the visual target) of the display position of the visual target displayed on the display. For example, the control section can apply (set) the base direction of the prism by changing the display direction of the visual target displayed on the display.

For example, in a case where the prism is applied by changing the display position of the visual target, a table may be created in which the prism power and the base direction are set in advance in accordance with the display position of the visual target, and the created table may be stored in the memory. In this case, for example, the control section may call the display position of the visual target from the memory based on the prism information, and change the display position of the visual target. In addition, for example, regarding the display position of the visual target, an arithmetic expression for calculating the display position of the visual target may be stored in the memory in accordance with the prism power and the base direction, and the display position of the visual target may be obtained using the arithmetic expression.

In addition, for example, as a configuration for applying the prism to the examinee's eye, control using the light deflection section and change of the position of the visual target displayed on the display may be used in combination. According to this, it is possible to apply the prism that cannot be applied only by controlling either the control of the light deflection section or the display control. As an example, in a case where is applied by controlling the light deflection section and 3 Δ is applied by the display control, 8 Δ prism can be applied to the examinee's eye.

Example

Hereinafter, the subjective optometry apparatus of the present example will be described. For example, the subjective optometry apparatus may include subjective measurement means. In addition, for example, the subjective optometry apparatus may include objective measurement mean. In addition, in the present example, the subjective optometry apparatus provided with both the subjective measurement means and the objective measurement means will be described as an example.

FIG. 1 illustrates an exterior view of the subjective optometry apparatus 1 according to the present example. For example, the subjective optometry apparatus 1 includes a housing 2, a presentation window 3, a monitor 4, a chin mount 5, a base 6, an anterior ocular segment capture optical system 100, and the like. For example, the housing 2 includes a measurement section 7 on the inside thereof (details thereof will be described later). For example, the presentation window 3 is used to present the visual target to an examinee. For example, the target light flux from the measurement, section 7 is projected onto an examinee's eye E of the examinee via the presentation window 3.

For example, the monitor (display) 4 displays the optical characteristics result (for example, spherical refractivity S, cylindrical refractivity C, astigmatic axis angle A, and the like) of the examinee's eye E. For example, the monitor 4 is a touch panel. In other words, in the present example, the monitor 4 functions as an operation section (controller). For example, the signal that corresponds to an operation instruction input from the monitor 4 is output to the control section 70 which will be described later. In addition, the monitor 4 may not be a touch panel type, or may be configured to separately provide the monitor 4 and the operation section. For example, in this case, the operation section may be configured to use at least one operation section, such as a mouse, a joystick, or a keyboard.

For example, the monitor 4 may be a display mounted on the housing 2, or may be a display connected to the housing 2. For example, in this case, a configuration using the display of a personal computer may be used. In addition, for example, a plurality of displays may be used together.

For example, the distance between the examinee's eye E and the subjective optometry apparatus 1 is kept constant by the chin mount 5. In the present example, the configuration using the chin mount 5 is used as an example to keep the distance between the examinee's eye E and the subjective optometry apparatus 1 constant, but the invention is not limited thereto. For example, in the present example, a configuration may be adopted in which a forehead protector, a face protector, and the like are used in order to keep the distance between the examinee's eye F and the subjective optometry apparatus 1 constant, for example, the chin mount 5 and the housing 2 are fixed to the base 6.

For example, the anterior ocular segment image capture optical system 100 is configured with an image capture element and a lens which are not illustrated in the drawing. For example, the anterior ocular segment image capture optical system 100 is used to capture an image of the face of the examinee.

<Measurement Section>

For example, the measurement section 7 includes a left eye measurement section 7L and a right eye measurement section 7R. For example, the left eye measurement section 7L and the right eye measurement section 7R in the present example include the same member. In other words, the subjective optometry apparatus 1 in the present example includes a pair of left and right subjective measurement sections and a pair of left and right objective measurement means. Naturally, the left eye measurement section 7L and the right eye measurement section 7R may be configured such that at least some members thereof are different from each other.

Figure 2:
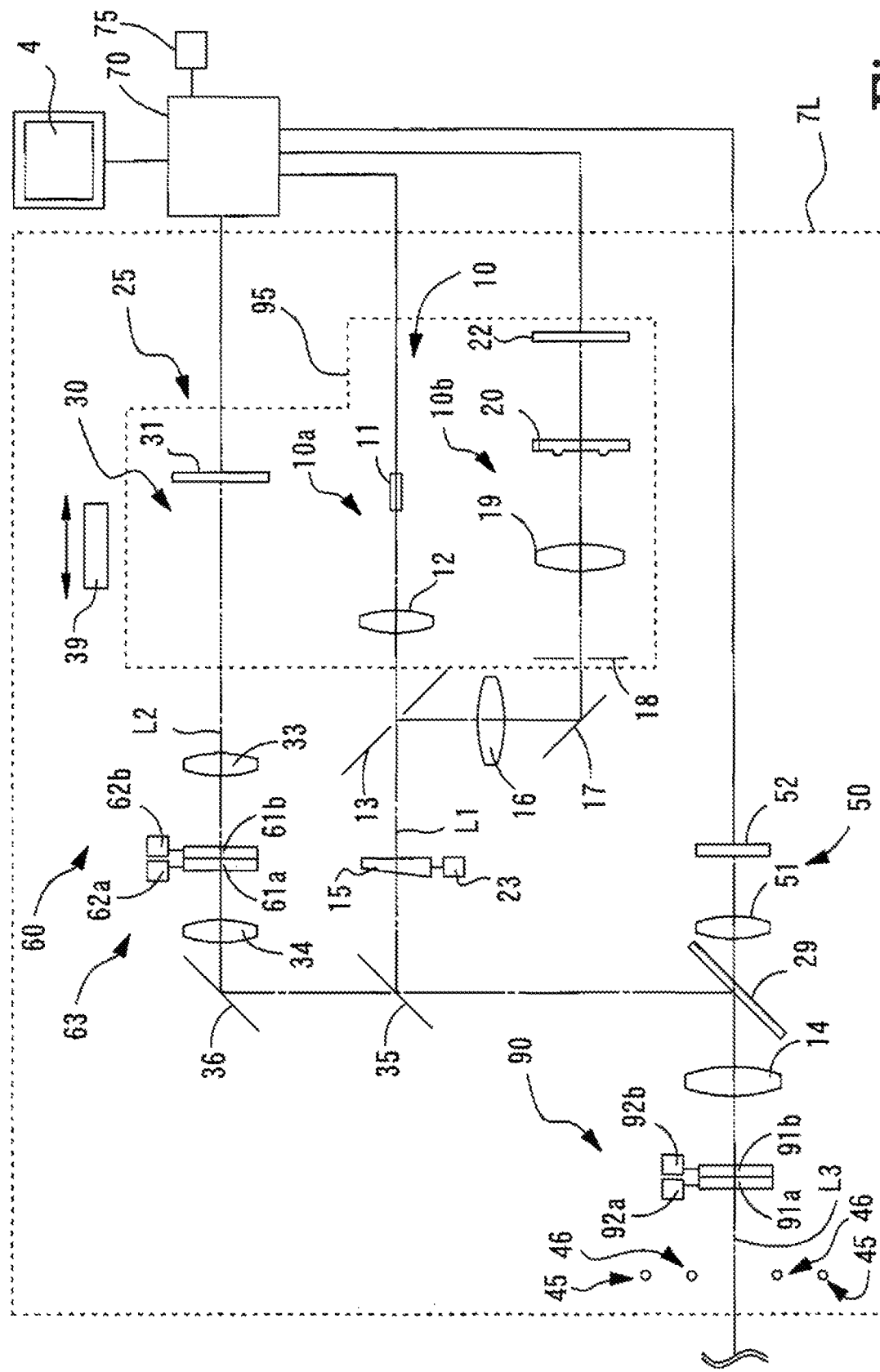
FIG. 2 is a view illustrating a configuration of a measurement section.

FIG. 2 is a view illustrating a configuration of the measurement section 7. For example, in the present example, the left eye measurement section 7L is described as an example. In addition, since the right eye measurement section 7R has the same configuration as that of the left eye measurement section 7L, the description thereof will be omitted. For example, the left eye measurement section 7L includes the subjective measurement optical system 25, the objective measurement optical system 10, the first index projection optical system 45, the second index projection optical system 46, and the observation optical system 50.

<Subjective Optical System>

For example, the subjective measurement optical system 25 is used as a part of the configuration of the subjective measurement means for subjectively measuring optical characteristics of the examinee's eye E (details thereof will be described later). Examples of the optical characteristics of the examinee's eye E include an eye refractive power, a contrast sensitivity, a binocular vision function (for example, the amount of oblique position, a stereoscopic visual function, and the like), and the like. In addition, in the present example, an example of the subjective measurement means for measuring the eye refractive power of the examinee's eye E will be described. For example, the subjective measurement optical system 25 includes the light projecting optical system (visual target projection system) 30, the calibration optical system 60, and a correction optical system 90.

For example, the light projecting optical system 30 projects the target light flux toward the examinee's eye E. For example, the light projecting optical system 50 includes the display 31, a projection lens a projection lens 34, a reflecting mirror 36, a dichroic mirror 35, a dichroic mirror 29, and an objective lens 14. For example, the target light flux projected from the display 31 is projected onto the examinee's eye E through the optical member in order of the projection lens 33, the projection lens 34, the reflecting mirror 36, the dichroic mirror 35, the dichroic mirror 29, and the objective lens 14.

For example, an examination visual target, such as a Landolt ring visual target, a fixation target for fixedly viewing the examinee's eye E, and the like are displayed on the display 31. For example, the target light flux from the display 31 is projected toward the examinee's eye E. For example, in the present example, the following description will be given by taking a case where a liquid crystal display (LCD) is used as the display 31 as an example. In addition, as a display, an organic electro luminescence (EL) display, a plasma display, or the like can also be used.

For example, the calibration optical system 60 is disposed in the optical path of the light projecting optical system 30. For example, the calibration optical system 60 changes the optical characteristics of the target light flux. For example, the calibration optical system 60 includes an astigmatism calibration optical system 63 and a dining mechanism 39. For example, the astigmatism calibration optical system 63 is disposed between the projection lens 34 and the projection lens 33. For example, the astigmatism calibration optical system 63 is used for calibrating a cylindrical power, a cylindrical axis (astigmatic axis), and the like of the examinee's eye E. For example, the astigmatism calibration optical system 63 is configured with two positive cylindrical lenses 61a and 61b having the same focal distance. The cylindrical lenses 61a and 61b are independently rotated around an optical axis L2 by the driving of respective rotation mechanisms 62a and 62b. Meanwhile, in the present example, the astigmatism calibration optical system 63 has been described using an example of a configuration in which the two positive cylindrical lenses 61a and 61b are used, but the invention is not limited thereto. The astigmatism calibration optical system 63 may be configured to be capable of calibrating a cylindrical power, a cylindrical axis, and the like. In this case, a configuration may also be adopted in which the calibration lens is inserted into and removed from the optical path of the light projecting optical system 30.

For example, the driving mechanism 39 is configured with a motor and a slide mechanism. For example, by the driving mechanism 39, the display 31 is integrally moved in the direction of the optical axis L2. For example, the presentation position (presenting distance) of the visual target with respect to the examinee's eye E is optically changed by the movement of the display 31 during the subjective measurement, and a spherical refractive power of the examinee's eye E is calibrated. In other words, the calibration optical system of the spherical power is configured by the movement of the display 31. In addition, for example, fogging is applied to the examinee's eye E by the movement of the display 31 during the objective measurement. Meanwhile, the calibration optical system of the spherical power is not limited thereto. For example, the calibration optical system of the spherical power includes a large number of optical elements, and may be configured to perform calibration by the optical elements being disposed in the optical path. In addition, for example, the calibration optical system of the spherical power may be configured to move the lens disposed in the optical path in the optical axis direction.

Meanwhile, in the present example, a description has been given of an example of a configuration in which the astigmatism calibration optical system 63 for calibrating the cylindrical power and the cylindrical axis (astigmatic axis) and the calibration optical system (for example, the driving section 39) for calibrating the spherical power are separately provided, but the invention is not limited thereto. For example, as the calibration optical system, a configuration may be adopted in which a calibration optical system for calibrating a spherical power, a cylindrical power, and an astigmatic axis is provided. In other words, the calibration optical system in the present example may be an optical system for modulating the wavefront. In addition, for example, the calibration optical system may be an optical system that calibrates a spherical power, a cylindrical power, an astigmatic axis, and the like. In this case, for example, the calibration optical system may be configured to include a lens disc on which a large number of optical elements (a spherical lens, a cylindrical lens, and the like) are disposed on the same circumference. The lens disc is rotationally controlled by the driving section (actuator and the like), and the optical element (for example, a cylindrical lens and a cross cylinder lens) desired by the examiner is disposed on the optical axis 12 at the rotation angle desired by the examiner. For example, the switching of the optical element disposed on the optical axis 12, and the like may be performed by the operation of the monitor 4 or the like.

The lens disc is configured with one lens disc or a plurality of lens discs. In a case where a plurality of lens discs are disposed, the driving section that corresponds to each of the lens discs is provided. For example, as a lens disc group, each of the lens discs has an opening (or a 0 D lens) and a plurality of optical elements. As a type of each of the lens discs, a spherical lens disc having a plurality of spherical lenses with different frequencies, a cylindrical lens disc having a plurality of cylindrical lenses with different, frequencies, and an auxiliary lens disc, having a plurality of types of auxiliary lenses are representative. At least one of a red filter and a green filter, a cross cylinder lens, a polarizing plate, a Maddox lens, and an autocross cylinder lens is disposed on the auxiliary lens disc. In addition, the cylindrical lens is rotatably disposed around the optical axis L2 by the driving section, and the cross cylinder lens may be disposed to be rotatable around each of the optical axes by the driving section.

For example, the correction optical system 90 is disposed between the objective lens 14 and the deflection mirrors 81 which will be described later. For example, the correction optical system 90 is used for correcting optical aberrations (for example, astigmatism) generated in the subjective measurement. For example, the correction optical system 90 is configured with two positive cylindrical lenses 91a and 91b having the same focal length. For example, the correction optical system 90 corrects the astigmatism by adjusting the cylindrical power and the astigmatic axis. Each of the cylindrical lens 91a and the cylindrical lens 91b is independently rotated around an optical axis L3 by driving the rotation mechanisms 92a and 92b, respectively. In addition, in the present example, the configuration using two positive cylindrical lenses 91a and 91b has been described as an example of the correction optical system 90, but the present invention is not limited thereto. The correction optical system 90 may have any configuration as long as the configuration can correct the astigmatism. In this case, for example, the correction lens may be inserted into and removed from the optical axis L3.

In addition, in the present example, the configuration in which the correction optical system 90 is disposed separately from the calibration optical system 60 has been described as an example, but the present invention is not limited thereto. For example, the calibration optical system 60 may be configured to also serve as the correction optical system 90. In this case, the cylindrical power of the examinee's eye E and the cylindrical axis (astigmatic axis) are corrected in accordance with the amount of astigmatism. In other words, the calibration optical system 60 is driven so as to correct the cylindrical power considering (correcting) the astigmatism amount or the astigmatic axis. For example, by using both the calibration optical system 60 and the corrects on optical system 90, complicated control is not required, and thus, it is possible to correct the optical aberration with a simple configuration. In addition, for example, by using both the calibration optical system 60 and the correction optical system 90, it is not necessary to separately provide the correction optical system for the optical aberration, and thus, it is possible to correct the optical aberration with a simple configuration.

<Objective Optical System>

For example, the objective measurement optical system 10 is used as a part of a configuration of the objective measurement means for objectively measuring the optical characteristics of the examinee's eye (details thereof will be described later). Examples of the optical characteristics of the examinee's eye include an eye refractive power, an ocular axial length, a cornea shape, and the like, in the example, an example of the objective measurement means for measuring an eye refractive power of the examinee's eye will be described. For example, the objective measurement optical system 10 includes a projection optical system 10a, a light receiving optical system 10b, and a correction optical system 90.

For example, the projection optical system (light projecting optical system) 10a projects a spot-shaped measurement index onto the fundus of the examinee's eye E through the pupil center portion of the examinee's eye E. For example, the light receiving optical system 10b extracts fundus reflected light reflected from the fundus in a ring shape through a pupil peripheral portion, and causes a two-dimensional image capture element 22 to capture a ring-shaped fundus reflected image.

For example, the projection optical system 10a includes a measurement light source 11, a relay lens 12, a hole mirror 13, a prism 15, a driving section (motor) 23, a dichroic mirror 35, a dichroic mirror 29, and an objective lens 14 which are disposed on an optical axis L1 of the objective measurement optical system 10. For example, the prism 15 is a luminous flux deflection member. For example the driving section 23 rotationally drives the prism 15 around the optical axis L1. For example, the light source 11 has a conjugate relationship with the fundus of the examinee's eye E. Further, the hole portion of the hole mirror 13 has a conjugate relationship with the pupil of the examinee's eye E. For example, the prism 15 is disposed at a position away from the position conjugated with the pupil of the examinee's eye E, and the luminous flux to pass through the prism is eccentric with the optical axis L1. Meanwhile, a configuration may also be adopted in which a parallel plane plate is obliquely disposed on the optical axis L1 as the luminous flux deflection member instead of the prism 15.

For example, the dichroic mirror 35 is common to the optical path of the subjective measurement optical system 25 and the optical path of the objective measurement optical system 10. In other words, for example, the dichroic mirror 35 has the optical axis L2 of the subjective measurement optical system 25 and the optical axis L1 of the objective measurement optical system 10 as the same axis, for example, the dichroic mirror 29 which is an optical path branching member reflects the luminous flux of the subjective measurement optical system 25 and the measurement light of the projection optical system 10a, and guides the reflected luminous flux and measurement light to the examinee's eye E.

For example, the light receiving optical system 10b uses the objective lens 14, the dichroic mirror 29, the dichroic mirror 35, the prism 15, and the hole mirror 13 in common with the projection optical system 10a, and includes a relay lens 16 disposed in the optical path in the reflection direction of the hole mirror 13, a mirror 17, a light receiving diaphragm 18 disposed in the optical path in the reflecting direction of the mirror 17, a collimator lens 19, a ring lens 20, and the two-dimensional image capture element 22, such as a CCD. For example, the light receiving diaphragm 18 and the two-dimensional image capture element 22 has a conjugate relationship with the fundus of the examinee's eye E. For example, the ring lens 20 is configured with a lens portion formed in a ring shape and a light shielding portion obtained by performing coating for light shielding in a region other than the lens portion, and has an optically conjugate positional relationship with the pupil of the examinee's eye E. For example, an output from the two-dimensional image capture element 22 is input to the control section 70.

For example, the dichroic mirror 29 reflects the reflected light of the measurement light from the projection optical system 10a guided to the fundus of the examinee's eye E toward the light receiving optical system 10. In addition, feu example, the dichroic mirror 29 transmits anterior ocular segment observation light and alignment light, and guides the transmitted light to the observation optical system 50. For example, the dichroic mirror reflects the reflected light of the measurement light from the projection optical system 10a guided to the fundus of the examinee's eye E toward the light receiving optical system 10.

Meanwhile, the objective measurement optical system 10 is not limited to the above-described objective measurement optical system, and it is possible to use a well-known objective measurement optical system configured to project a ring-shaped measurement index onto the fundus from the pupil peripheral portion, to extract the fundus reflected light from the pupil center portion, and to cause the two-dimensional image capture element 22 to receive light of the ring-shaped fundus reflected image.

Meanwhile, the objective measurement optical system 10 is not limited to the above-described objective measurement optical system, and may be a measurement optical system including a light projecting optical system which projects the measurement light toward the fundus of the examinee's eye E and a light receiving optical system in which the reflected light acquired by the reflection of the measurement light from the fundus is received by a light receiving element. For example, an eye refractive power measurement optical system may be configured to include a Shack Hartman sensor. Naturally, an apparatus using another measurement method may be used (for example, an apparatus of a phase difference system which projects a slit).

For example, the light source 11 of the projection optical system 10a, and the light receiving diaphragm 18, the collimator lens 19, the ring lens 20, and the two-dimensional image capture element 22 of the light receiving optical system 10b can be integrally moved in the optical axis direction. In the present example, for example, the light source 11 of the projection optical system 10a and the light receiving diaphragm 18, the collimator lens 19, the ring lens 20, and the two-dimensional image capture element 22 of the light receiving optical system 10b are integrally moved in the direction of the optical axis L1 by the driving mechanism 39 that drives the display 31. In other words, the display 31, the light source 11 of the projection optical system 10a, the light receiving diaphragm 18, the collimator lens 19, the ring lens 20, and the two-dimensional image capture element 22 of the light receiving optical system 10b are integrally moved as a driving unit 95 in synchronization with each other. Naturally, a configuration in which the components are separately driven may also be adopted.

For example, the driving unit 95 moves a part of the objective measurement optical system 10 in the optical axis direction such that an external ring luminous flux is incident on the two-dimensional image capture element 22 with respect to each longitudinal direction. In other words, a part of the objective measurement optical system 10 is moved in the direction of the optical axis L1 in accordance with a spherical refractive error (spherical refractive power) of the examinee's eye E, such that the spherical refractive error is corrected and the light source the light receding diaphragm 18, and the two-dimensional image capture element 22 are optically conjugated with the fundus of the examinee's eye E. For example, the position of the driving mechanism 39 to be moved is detected by a potentiometer not illustrated in the drawing. Meanwhile, the hole mirror 13 and the ring lens 20 are disposed so as to be conjugated with the pupil of the examinee's eye F with a fixed magnification, regardless of the amount of movement of the driving unit 95.

In the above-described configuration, measurement luminous flux emitted from the light source 11 forms a spot-shaped point light source image on the fundus of the examinee's eye E through the relay lens 12, the hole mirror 13, the prism 15, the dichroic mirror 35, the dichroic mirror 29, and the objective lens 14. At this time, a pupil projection image (projected luminous flux on the pupil) of the hole portion in the hole mirror 13 is eccentrically rotated at high speed by the prism 15 rotating around the optical axis. The point light source image projected onto the fundus is reflected and scattered, is emitted from the examinee's eye E, is collected by the objective lens 14, and is collected again at the position of the light receiving diaphragm 18 through the dichroic mirror 29, the dichroic mirror 35, the prism 15 which rotates at high speed, the hole mirror 13, the relay lens 16, and the mirror 17, thereby forming a ring-shaped image on the two-dimensional image capture element 22 by the collimator lens 19 and the ring lens 20.

For example, the prism 15 is disposed in an optical path which is common to the projection optical system 10a and the light receiving optical system 10b. For example, a reflected luminous flux from the fundus passes through the prism 15 which is the same as that of the projection optical system 10a, and thus, backward scanning is performed as if there is no eccentricity of the projected luminous flux and the reflected luminous flux (received luminous flux) on the pupil in the subsequent optical systems.

For example, the correction optical system 90 also serves as the subjective measurement optical system 25. Naturally, a configuration may also be adopted in which a correction optical system used in the objective measurement optical system 10 is separately provided.

<First Index Projection Optical System and Second Index Projection Optical System>

For example, in the present example, the first index projection optical system 45 and the second index projection optical system 46 are disposed between the correction optical system 90 and the deflection mirrors 81. Naturally, the arrangement position of the first index projection optical system 45 and the second index projection optical system 46 are not limited thereto. For example, the first index projection optical system 45 and the second index projection optical system 46 may be provided in a cover of the housing 2. For example, in this case, the first index projection optical system 45 and the second index projection optical system 46 are arranged around the presentation window 3.

For example, to the first index projection optical system 45, a plurality of infrared light sources are disposed on the concentric circle around the optical axis L3 at intervals of 45 degrees, and are disposed so as to be bilaterally symmetrical to each other with a vertical plane passing through the optical axis L3 therebetween. For example, the first index projection optical system 45 emits near infrared light for projecting an alignment index onto the cornea of the examinee's eye E. For example, the second index projection optical system 46 includes six infrared light sources which are disposed at a position different from the position of the first index projection optical system 45. In this case, the first index projection optical system 45 is configured to project an index at an infinite distance onto the cornea of the examinee's eye E from the left-right direction, and the second index projection optical system 46 is configured to project an index at a finite distance onto the cornea of the examinee's eye E from the up-down direction or an oblique direction. Meanwhile, in FIG. 2, only a part of the first index projection optical system 45 and the second index projection optical system 46 is illustrated for convenience of description. Meanwhile, the second index projection optical system 46 is also used as an anterior ocular segment illumination that illuminates the anterior ocular segment of the examinee's eye E. In addition, the second index projection optical system 46 can also be used as an index for measuring the shape of the cornea. In addition, the first index projection optical system 45 and the second index projection optical system 46 are not limited to a dot-shaped light source. For example, the systems may be a ring-shaped light source or a linear light source.

<Observation Optical System>

For example, the observation optical system (image capture optical system) 50 shares the objective lens 14 and the dichroic mirror 20 in the subjective measurement optical system 25 and the objective measurement optical system 10, and includes an imaging lens 51 and a two-dimensional image capture element 52. For example, the image capture element 52 has an imaging surface disposed at a position substantially conjugated with the anterior ocular segment of the examinee's eye E. For example, an output from the image capture element 52 is input to the control section 70. Accordingly, an anterior ocular segment image of the examinee's eye B is captured by the two-dimensional image capture element 52 and is displayed on the monitor 4. Meanwhile, the observation optical system 50 also serves as an optical system that detects an alignment index image formed on the cornea of the examinee's eye E by the first index projection optical system 45 and the second index projection optical system 46, and the position of the alignment index image is detected by the control section 70.

<Internal Configuration of Subjective Optometry Apparatus>

Figure 3:
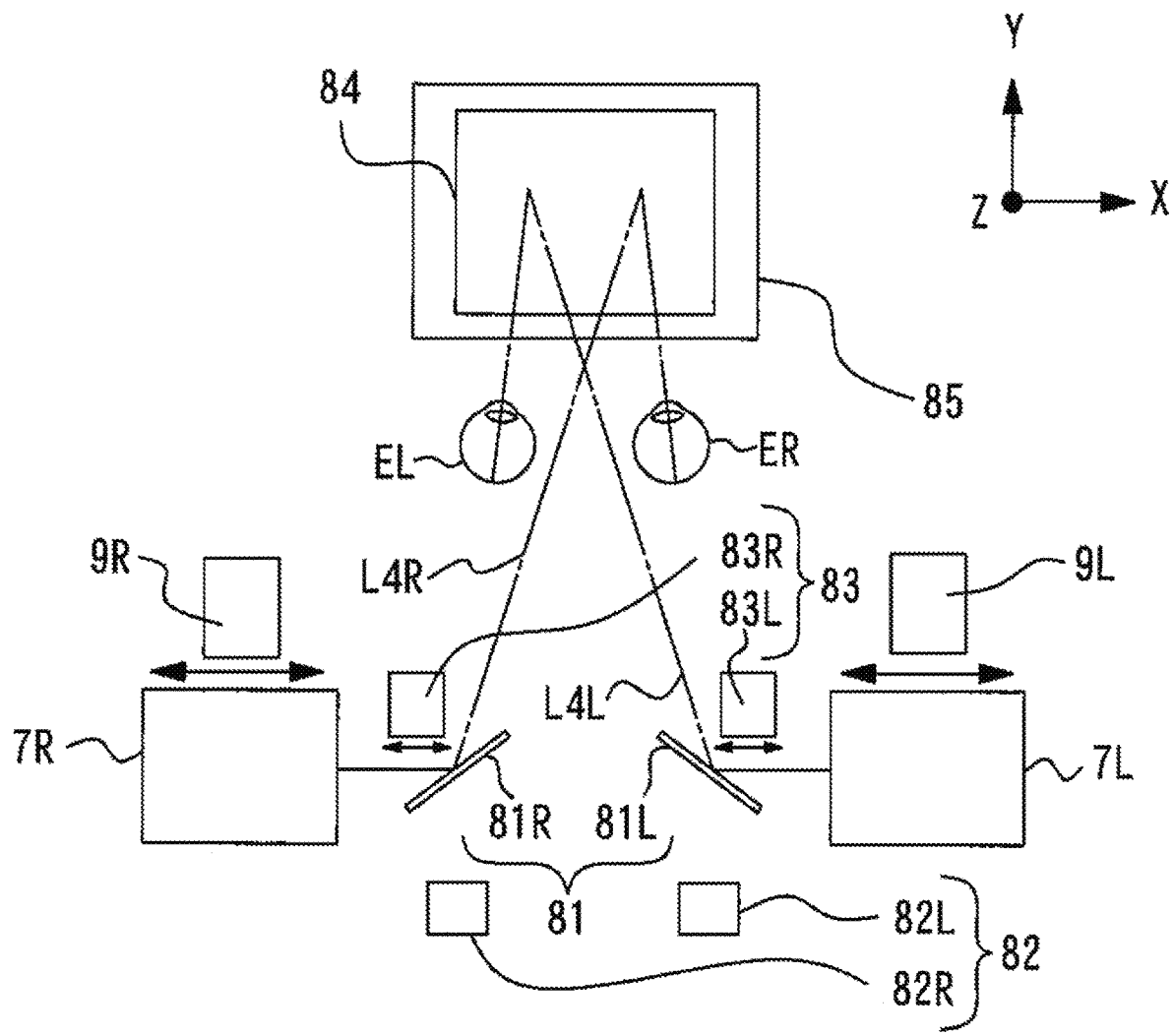
FIG. 3 is a schematic configuration view of the inside of the subjective optometry apparatus when seen from the front.
Figure 4:
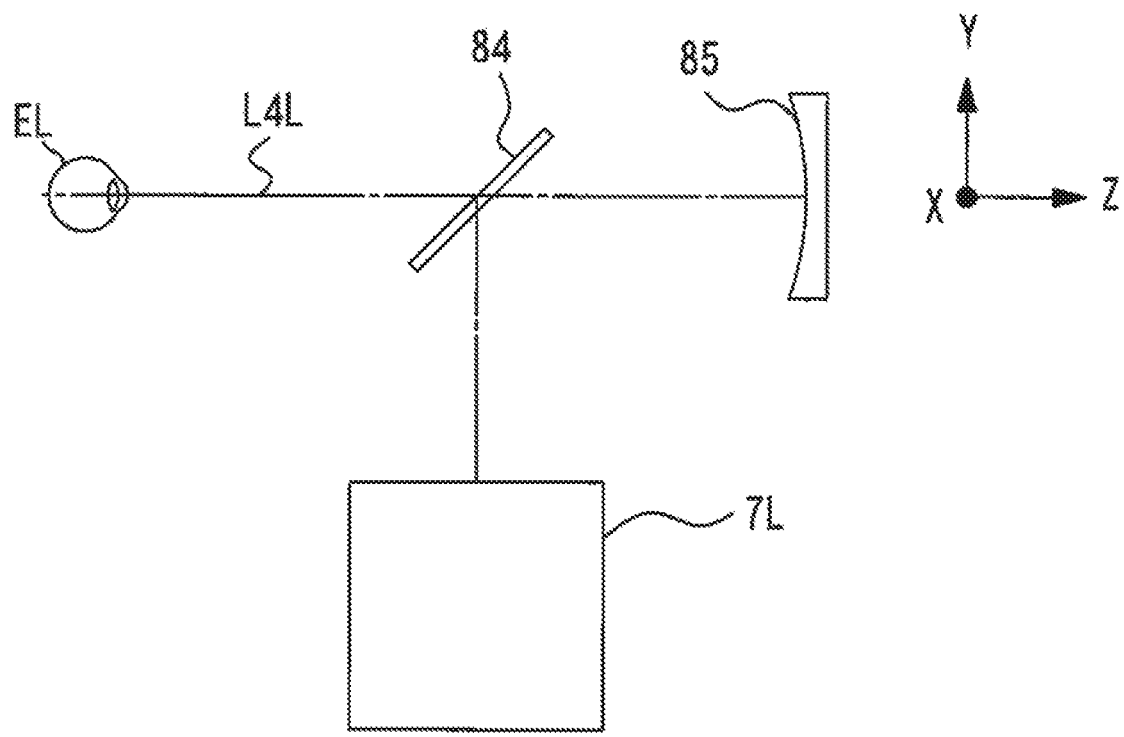
FIG. 4 is s schematic configuration view of the inside of the subjective optometry apparatus when seen from the side.
Figure 5:
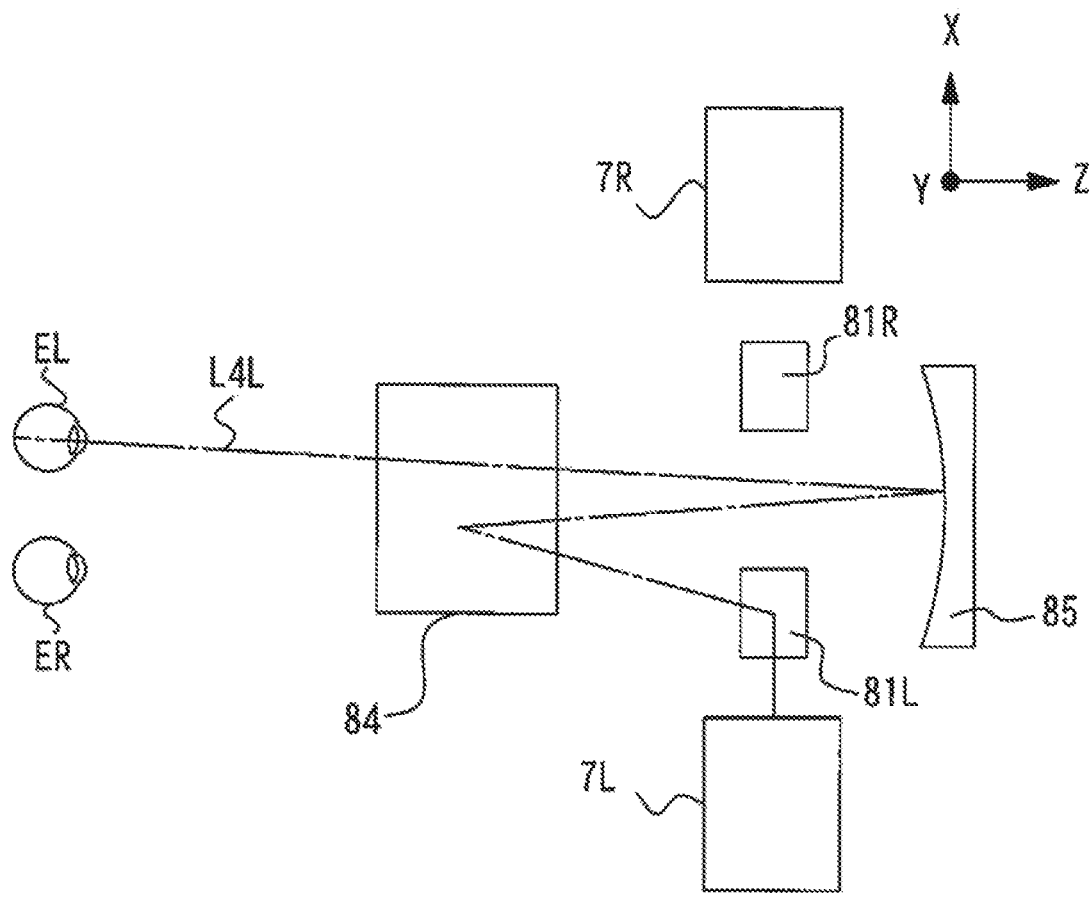
FIG. 5 is a schematic configuration view of the inside of the subjective optometry apparatus when seen from above.

Hereinafter, the internal configuration of the subjective optometry apparatus 1 will be described. FIG. 3 is a schematic configuration view of the inside of the subjective optometry apparatus 1 according to the present example when it is seen from the front (a direction A of FIG. 1). FIG. 4 is a schematic configuration view of the inside of the subjective optometry apparatus 1 according to the present example when it is seen from the side (a direction B of FIG. 1). FIG. 5 is a schematic configuration view of the inside of the subjective optometry apparatus 1 according to the present example when it is seen from above (a direction C of FIG. 1). Meanwhile, in FIG. 3, an optical axis indicating reflection by a half mirror 84 is omitted for convenience of description. In addition, in FIG. 4, only the optical axis of the left eye measurement section 7L is illustrated for convenience of description. Further, in FIG. 5, only the optical axis of the left eye measurement section 7L is illustrated for convenience of description.

For example, the subjective optometry apparatus 1 includes subjective measurement means and objective measurement means. For example, the subjective measurement means includes the measurement section 7, the deflection mirrors 81, the driving sections 82, the driving sections 83, the half mirror 84, and the concave surface mirror 85. Naturally, the subjective measurement means is not limited to such a configuration. As an example, the configuration without the half mirror 84 may be adopted. In this case, the optical axis of the concave surface mirror 85 may be irradiated with the luminous flux obliquely, and the reflected luminous flux may be guided to the examinee's eye F. For example, the objective measurement means is confirmed with the measurement section 7, the deflection mirrors 81, the half mirror 84, and the concave surface mirror 85. Naturally, the objective measurement means is not limited to such a configuration. As an example, the configuration without the half mirror 84 may be adopted. In this case, the optical axis of the concave surface mirror 85 may be irradiated with the luminous flux obliquely, and the reflected luminous flux may be guided to the examinee's eye E.

For example, the subjective optometry apparatus 1 includes a left eye driving section 9L and a right eye driving section 9R, and the left eye measurement section 7L and the light eye measurement section 7R can be moved in the X direction. For example, the left eye measurement section 7L and the right eye measurement section 7R are moved, and thus a distance between the deflection mirrors 81 and the measurement section 7 is changed, and the presentation position of the target light flux in the Z direction is changed. Accordingly it is possible to guide the target light flux calibrated by the calibration optical system 60 to the examinee's eye E and to adjust the measurement section 7 in the Z direction such that the image of the target light flux calibrated by the calibration optical system 60 is formed on the fundus of the examinee's eye E.

For example, the deflection mirrors 81 includes a right eye deflection mirror 81R and a left eye deflection mirror 81L which are provided in a left and right pair respectively. For example, the deflection mirrors 81 is disposed between the calibration optical system 60 and the examinee's eye E. In other words, the calibration optical system 60 includes the right eye calibration optical system and the left eye calibration optical system which are provided in a left and right pair, the left eye deflection mirror 81L is disputed between the left eye calibration optical system and a left eye ER, and the right eye deflection mirror 81R is disposed between the right eye calibration optical system and a right eye ER. For example, it is preferable that the deflection mirrors 81 are disposed at a position conjugated with the pupil.

For example, the left eye deflection mirror 81L reflects a luminous flux projected from the left eye measurement section 7L, and guides the luminous flux to the examinee's left eye EL. In addition, for example, the left eye deflection mirror 81L reflects the reflected light reflected by the examinee's left eye EL, and guides the reflected light to the left eye measurement section 7L. For example, the light eye deflection mirror 81R reflects the luminous flux projected from the right eye measurement section 7R and guides the luminous flux to the examinee's right eye ER. In addition, for example, the right eye deflection mirror 81R reflects the reflected light reflected by the examinee's right, eye ER, and guides the reflected light to the right eye measurement section 7R. Meanwhile, in the present example, a description has been given of an example of a configuration in which the deflection mirrors 81 are used as a deflection member that reflects the luminous flux projected from the measurement section 7 and guides the luminous flux to the examinee s eye E, but the invention is not limited thereto. As the deflection member, any deflection member that reflects the luminous flux projected from the measurement section 7 and guides the luminous flux to the examinee's eye E may be used. Examples of the deflection member include a prism, a lens, or the like.

For example, the driving sections 82 are configured with a motor (driving section) or the like. For example, the driving sections 82 include a driving section 82L for driving the left eye deflection mirror 81L and a dining section 82R for driving the right eye deflection mirror 81R. For example, the deflection mirrors 81 are rotated and moved by the driving of the driving sections 82. For example, the driving sections 82 rotate the deflection mirrors 81 around a rotation axis in the horizontal direction (X direction) and a rotation axis in the vertical direction (Y direction). In other words, the driving sections 82 rotate the deflection mirrors 8*t* in the XY directions. Meanwhile, the rotation of the deflection mirrors 81 may be performed in either the horizontal direction or the vertical direction.

For example, the driving sections 83 are configured with a motor (driving section) or the like. For example, the driving sections 83 include a driving section 83L for driving (be left eye deflection mirror 81L and a driving section 83R for driving the right eye deflection mirror 81R. For example, the deflection mirrors 81 are moved in the X direction in the driving of the driving sections 83. For example, a distance between the left eye deflection mirror 81L and the right eye deflection mirror 81R is changed by the movement of the left eye deflection mirror 81L and the right eye deflection mirror 81R, and thus it is possible to change a distance between a left eye optical path and a right eye optical path in the X direction in accordance with the pupillary distance of the examinee's eye E.

Meanwhile, for example, a plurality of deflection mirrors may be provided in each of the left eye optical path and the right eye optical path. Examples of the configuration include a configuration in which two deflection mirrors are provided in each of the left eye optical path and the right eye optical path (for example, two deflection mirrors in the left eye optical path, or the like). In this case, one deflection mirror may be rotated in the X direction, and the other deflection mirror may be rotated in the Y direction. For example, the deflection mirrors 81 are rotated and moved, and thus it is possible to optically correct the position of an image to be formed by deflecting an apparent luminous flux for the image of the calibration optical system 60 to be formed in front of the examinee's eye.

For example, the concave surface mirror 85 is shared by the right eye measurement section 7R and the left eye measurement section 7L. For example, the concave surface mirror 85 is shared by the right eye optical path including the right eye calibration optical system and the left eye optical path including the left eye calibration optical system. In other words, the concave surface mirror 85 is disposed at a position where the concave surface mirror passes through both the right eye optical path including the right eye calibration optical system and the left eye optical path including the left eye calibration optical system. Naturally, the concave surface mirror 85 may be configured not to be shared by the right eye optical path and the left eye optical path. In other words, a configuration may also be adopted in which the concave surface mirrors are provided in each of the right eye optical path including the right eye calibration optical system and the left eye optical path including the left eye calibration optical system. For example, the concave surface mirror guides the target light flux having passed through the calibration optical system to the examinee's eye E, and forms an image of the target light flux having passed through the calibration optical system in front of the examinee's eye E. In addition, in the present embodiment, the configuration using the concave surface mirror 85 has been described as an example, but the invention is not limited thereto, and various optical members can be used. For example, as the optical member, a lens, a planar mirror, and the like can be used.

For example, the concave surface mirror 85 also serves as the subjective measurement means and the objective measurement means. For example, the target light flux projected from the subjective measurement optical system 25 is projected onto the examinee's eye E through the concave surface mirror 85. For example, the measurement light projected from the objective measurement optical system 10 is projected onto the examinee's eye E through the concave surface mirror 85. In addition, for example, the reflected light of the measurement light projected from the objective measurement optical system 10 is guided to the light receiving optical system 10*b* of the objective measurement optical system 10 through the concave surface mirror 85. Meanwhile, in the present, example, a configuration in which the reflected light of the measurement light from the objective measurement optical system 10 is guided to the light receiving optical system 10*b* of the objective measurement optical system 10 through the concave surface mirror 85 has been described as an example, but the invention is not limited thereto. For example, a configuration may also be adopted in which the reflected light of the measurement light from the objective measurement optical system 10 does not go through the concave surface mirror 85.

In more detail, for example, in the present example, an optical axis between the concave surface mirror 85 and the examinee's eye E in the subjective measurement means and an optical axis between the concave surface mirror 85 and the examinee's eye E in the objective measurement means are configured as substantially the same axis. For example, in the present example, the optical axis L2 of the subjective measurement optical system 25 and the optical axis L1 of the objective measurement optical system 10 are combined with each other by the dichroic mirror 35, and are thus configured as the same axis.

<Optical Path of Subjective Measurement Means>

Hereinafter, the optical path of the subjective measurement means will be described. For example, the subjective measurement means reflects the target light flux having passed through the calibration optical system 60 in a direction of the examinee's eye by the concave surface mirror 85 to thereby guide the target light flux to the examinee's eye E, and forms an image of the target light flux having passed through the calibration optical system 60 in front of the examinee's eye E so as to optically have a predetermined examination distance. In other words, the concave surface mirror 85 reflects the target light flux so as to convert the target light flux into a substantially parallel luminous flux. Therefore, the visual target image seen from the examinee looks as if the visual target image is located farther than the actual distance between the examinee's eye E and the display 31. In other words, the concave surface mirror 85 is used, and thus it is possible to present the visual target image to the examinee such that the image of the target light flux is seen at the predetermined examination distance.

A more detailed description will be given. In the following description, the left eye optical path will be described as an example, but also in the right eye optical path, the same configuration as the configuration of the left eye optical path is adopted. For example, in the left eye subjective measurement means, the target light flux projected from the display 13 of the left eye measurement section 7L is incident on the astigmatism calibration optical system 63 through the projection lens 33. The target light flux having passed through the astigmatism calibration optical system 63 is incident on the correction optical system 90 through the reflecting mirror 30, the dichroic mirror 35, the dichroic mirror 29, and the objective lens 14. The target light flux having passed through the correction optical system 90 is projected toward the left eye deflection mirror 81L from the left eye measurement beet ion 71. The target light flux emitted from the left eye measurement section 7L and reflected by the left eye deflection mirror 81 is reflected toward the concave surface mirror 85 by the half mirror 84. The target light flux reflected by the concave surface mirror reaches the examinee's left eye EL through the half mirror 84.

Thereby, the visual target image calibrated by the calibration optical system 60 is formed on the fundus of the examinee's left eye EL based on a spectacle wearing position (for example, a position separated from the apex of the cornea at approximately 12 mm) of the examinee's left eye EL. Therefore, this is equivalent to the arrangement of the astigmatism calibration optical system 63 in front of the eyes and the adjustment of a spherical power by a calibration optical system (in the present example, driving of the driving mechanism 39) of a spherical power, and thus the examinee can collimate the visual target image in a natural state through the concave surface mirror 85. Meanwhile, in the present example, the right eye optical path also has the same configuration as that of the left eye optical path, and the visual target image calibrated by a pair of left and right calibration optical systems 60 is formed on the fundi of the examinee's both eyes, based on the spectacle wearing positions (for example, positions separated from the apexes of the corneas at approximately 12 mm) of the examinee's both eyes ER and EL. In this manner, the examinee responds to the examiner while looking straight at the visual target in a state of a natural sight, attempts calibration by the calibration optical system 60 until the examination visual target is seen properly, and subjectively measures the optical characteristics of the examinee's eye based on the calibration value thereof.

<Optical Path of Objective Measurement Means>

Subsequently, the optical path of the objective measurement means will be described. In the following description, the left eye optical path will be described as an example, but also in the right eye optical path, the same configuration as the configuration of the left eye optical path is adopted. For example, in the objective measurement means for the left eye, measurement light emitted from the light source 11 of the projection optical system 10a in the objective measurement optical system 10 is incident on the correction optical system 90 through the relay lens 12 to the objective lens 14. The measurement light having passed through the correction optical system 90 is projected toward the left eye deflection mirror 81L from the left eye measurement section 7L. The measurement light emitted from the left eye measurement section 7L and reflected by the left eye deflection mirror 81L is reflected toward the concave surface mirror 85 by the half mirror 84. The measurement light reflected by the concave surface mirror reaches the examinee's left eye EL through the half mirror 84, thereby forming a spot-shaped point light source image on the fundus of the examinee's left eye EL. At this time, a pupil projection image (projected luminous flux on the pupil) of the hole portion, of the hole mirror 13 is eccentrically rotated at high speed by the prism 15 rotating around the optical axis.

Light of the point light source image formed on the fundus of the examinee's left eye EL is reflected and scattered, and is emitted to the examinee's eye E, is collected by the objective lens 14 through the optical path through which the measurement light is transmitted, and passes through the dichroic mirror 29, the dichroic mirror 35, the prism 15, the hole mirror 13, the relay lens 16, and the mirror 17. The reflected light having passed through the components from the dichroic mirror to the mirror 17 is collected again on the opening of the light receiving diaphragm 18, is converted into a substantially parallel luminous flux (a case of a normal vision eye) by the collimator lens 19, is extracted as a ring-shaped luminous flux by the ring lens 20, and is received by the image capture element 22 as a ring image. The received ring image is analyzed, and thus it is possible to objectively measure the optical characteristics of the examinee's eye E.

<Control Section>

For example, various members, such as the monitor 4, a nonvolatile memory 75 (hereinafter, referred to as a memory 75), the measurement light source 11 included in the measurement section 7, the image capture element 22 the display and the two-dimensional image capture element are electrically connected to the control section 70. Further, for example, the driving sections which are not illustrated and are included in the driving; section 9, the driving mechanism the rotation mechanisms 62a and 62b, the driving sections 83, and the rotation mechanisms 92a and 92b are electrically connected to the control section 70.

For example, the control section 70 includes a CPU (processor), a RAM, a ROM, and the like. For example, the CPU controls each member of the subjective optometry apparatus 1. For example, the RAM temporarily stores various pieces of information. For example, various programs for controlling the operation of the subjective optometry apparatus 1, visual target data for various examinations, an initial value, and the like are stored in the ROM. Meanwhile, the control section 70 may be configured with a plurality of control sections (that is, a plurality of processors).

For example, the memory 75 is a non-fugitive storage medium capable of holding stored contents even when the supply of power is stopped. For example, as the memory 75, a USB memory or the like which is attachably and detachably mounted to a hard disc drive, a flash ROM, and the subjective optometry apparatus 1, can be used. For example, a control program for controlling the subjective measurement means and the objective measurement means is stored in the memory 75.

<Control Operation>

The operation of the subjective optometry apparatus 1 having the above-described configuration will be described. For example, in the present example, the objective measurement is performed with respect to the examinee's eye E by using the objective measurement optical system having the above-described configuration before the subjective measurement is performed. In this case, for example, the control section 70 acquires the objectively measured refractive power, such as the spherical refractivity S, the cylinder refractivity C, the astigmatic axis angle A, and the like of the examinee's eye E. In other words, the control section 70 acquires the objective eye refractive power (objective value) of the examinee's eye E. Further, for example, the control section stores the objective value in the memory 75. For example, in subjective measurement which will be described later, the calibration optical system 60 is controlled based on the acquired eye refractive power when the subjective measurement is performed, and the measurement is started with the state where the examinee's eye E has been corrected as an initial state.

Figure 6:
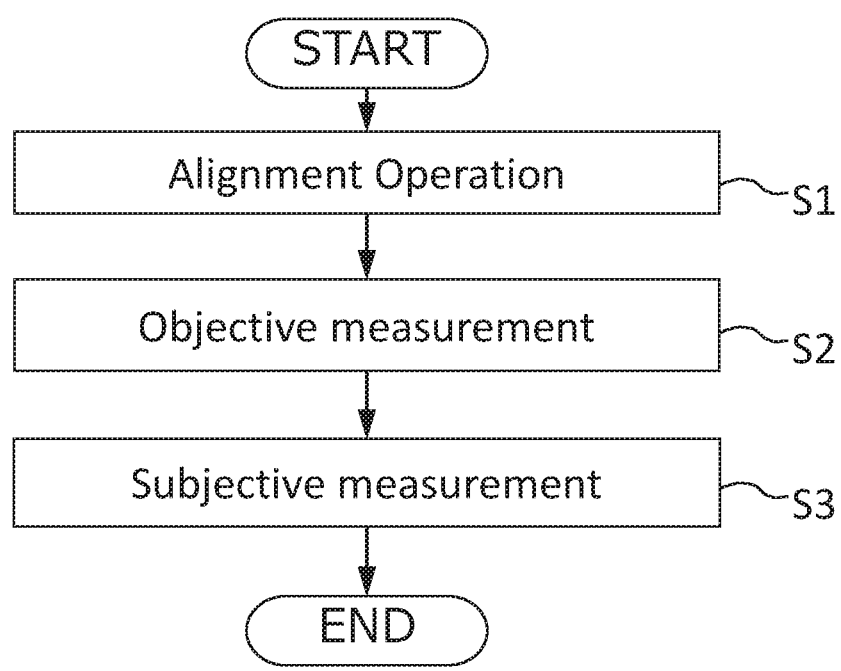
FIG. 6 is a flow chart illustrating a flow of a control operation.

For example, FIG. 6 is a flowchart illustrating a control operation in the present example. In the following, the description will be given in order based on the flowchart. In addition, in the present example, as a case where the examinee has an oblique position, a case where oblique position examination is performed as one example of binocular visual function examination will be described as an example.

<Alignment Operation (S1)>

For example, at the start of the subjective measurement, control of the calibration optical system 60 is performed in accordance with the eye refractive power of the examinee's eye E by using the above-described objective eye refractive power (objective value). For example, the control section 70 corrects the eye refractive power of the examinee's eye E by moving the display 31 in the direction of the optical axis L2 based on the objective eye refractive power acquired by the objective measurement. As an example, for example, in a case where the eye refractive power of the examinee's eye E is −4.0 D (diopter), the control section 70 moves the display 31 in the direction of the optical axis L2 so as to correct the eye refractive power of the examinee's eye E to 0 D.

Further, for example, the control section 70 may display a desired visual acuity value visual target (for example, a visual target having a visual acuity value of 1.0) on the display 31 as the initial presentation visual target. When the initial presentation visual target is presented to the examinee's eye E, the examiner performs far sight measurement of the examinee. For example, the examiner can switch the visual acuity value visual target displayed on the display by selecting a predetermined switch on the monitor 4. For example, the examiner performs switching to a visual target having a visual acuity value higher by one step in a case where the answer of the examinee is a correct answer. On the other hand, the examiner performs switching to a visual target having a visual acuity value lower by one step in a case where the answer of the examinee is a wrong answer. In other words, the control section 70 may switch the visual target displayed on the display 31 based on a signal for changing the visual acuity value from the monitor 4. Meanwhile, in the present example, far sight measurement will be described as an example, but the invention is not limited thereto. For example, regarding near sight measurement, measurements can be performed similar to the far sight measurement.

In addition, for example, at the start of subjective measurement, by using the pupillary distance of the examinee measured at the objective measurement, it is possible to change the distance in the X direction between the left eye optical path and the right eye optical path in accordance with the pupillary distance of the examinee's eye E. For example, the control section 70 drives the driving sections 83 based on the pupillary distance of the examinee's eye and moves the deflection mirrors HI in the X direction. For example, the distance between the left eye deflection mirror 81L and the right eye deflection mirror 81R is changed by the movement of the left eye deflection mirror 81L and the right eye deflection mirror 81R, and thus it is possible to change the distance between the left eye optical path and the right eye optical path in the X direction in accordance with the pupillary distance of the examinee's eye E. In addition, for example, the control section 70 changes the distance in the X direction between the left eye optical path and the right eye optical path in accordance with the pupillary distance of the examinee's eye E, and rotates the deflection mirrors 81. For example, the control section 70 drives the right eye deflection mirror 81R and the left eye deflection mirror 81L based on the pupillary distance, and rotates the mirrors in the X direction.

For example, with respect to the examinee, the examiner observes the presentation window 3 with the chin mounted on the chin mount 5, and instruct to fixate the visual target. For example, when the anterior ocular segment, of the examinee's eye E is detected by the anterior ocular segment capture optical system 100, the control section 70 starts aligning the examinee's eye E, and the measurement section 7. In other words, the control section 70 starts automatic alignment (S1). Meanwhile, in the present example, a case of measuring the optical characteristics of the examinee's eye in a case of the far sight will be described as an example. Similar to the far sight, it is also possible to measure the optical characteristics of the examinee's eye in a case of the near sight.

For example, the control section 70 detects the positions of each pupil of the examinee's left and right eyes from a face image captured by the capture optical system 100. For example, when the position of the pupil is detected, the control section 70 controls the subjective optometry apparatus 1 such that the anterior ocular segment image is displayed on the monitor A. For example, the control section 70 drives the right eye deflection mirror 81R and the left eye deflection mirror 81L, and rotates the mirrors in the XY directions. In addition, for example, when the position of the pupil is detected, the control section 7o can move the right eye measurement section 7R and the left eye measurement section 7L in the X direction. In other words, the control section 70 drives the deflection mirrors 81 to perform alignment in the XY directions, and drives the measurement section 7 to perform alignment in the Z direction. In addition, in the alignment in the Z direction, the control section 70 may drive the right eye deflection mirror 81R and the left eye deflection mirror 81L, and rotate the mirrors in the XY directions.

Meanwhile, in the present example, a description has been given of an example of a configuration in which alignment in the XYZ directions is adjusted by the driving of the deflection, mirrors 81 and the measurement section 7, but the invention is not limited thereto. Any configuration may also be adopted as long as a positional relationship between the examinee's eye, the subjective measurement means, and the objective measurement means can be adjusted. In other words, any configuration may also be adopted as long as the XYZ directions can be adjusted such that an image calibrated by the calibration optical system 60 is formed on the fundus of the examinee's eye. For example, a configuration may also be adopted in which the subjective optometry apparatus 1 is moved by providing a configuration in which the subjective optometry apparatus 5 can be moved in the XYZ directions with respect to the chin mount 6. In addition, for example, as a configuration in which the deflection mirrors 81 and a measurement unit, can be integrally moved in the XYZ directions, a configuration in which adjustment in the XYZ directions can be performed may be adopted. In addition, for example, a configuration may also be adopted in which adjustment in the XYZ directions can be performed only by the deflection mirrors 81. In this case, examples of the configuration include a configuration in which the deflection mirrors 81 is moved in the Z direction such that the deflection mirrors 81 is rotation ally driven and a distance between the deflection mirrors 81 and the measurement unit is changed. Meanwhile, for example, in the alignment control, examinee's both eyes may be displayed on the monitor 4, and the alignment control of the examinee's both eyes may be performed on the same screen. In addition, for example, in the alignment control, after one of the examinee's eyes is displayed on the monitor 4 and after the alignment control of the one of the examinee's eyes is completed, the other of the examinee's eyes may be displayed on the monitor 4, and the alignment control of the other of the examinee's eyes may be performed. In addition, for example, a configuration may also be adopted in which the alignment control of the other of the examinee's eyes may be performed based on an alignment control result of the one of the examinee's eyes.

For example, the control section 70 detects a deviation of the target light flux with respect to the examinee's eye. For example, the control section 70 detects a deviation (deviation between the examinee's eye and the optical axis of the light projecting optical system 30) of the image of the calibration optical system 60 with respect to the examinee's eye. For example, the control section 70 controls the driving section based on the detected detection result, and optically corrects the position of the image formed by deflecting an apparent luminous flux for guiding the image of the calibration optical system 60 to the examinee's eye. In this manner, the subjective optometry apparatus 1 in the present example has a configuration in which a deviation between the examinee's eye and the optical axis of the calibration optical system (optical axis of the light projecting optical system), and the position of the image formed is optically corrected. Thereby, the deviation between the examinee's eye and the optical axis of the light projecting optical system is corrected, and thus it is possible to use the apparatus at an appropriate position and to perform measurement with high accuracy.

<Objective Measurement (S2)>

The control section 70 emits an objective measurement start trigger signal (hereinafter, referred to as a trigger signal) for starting the objective measurement (objective measurement) (S2) based on the output of an alignment completion signal. When the trigger signal for starting the objective measurement is emitted, the control section 70 emits the measurement luminous flux from the objective measurement optical system 10. In this case, each measurement luminous flux is reflected by the concave surface mirror 85 through the deflection mirrors 81R and 81L, and is then projected onto the fundus of the examinee's eye. After the measurement light reflected from the fundus is reflected by the deflection mirror 81R (81L) through the concave surface mirror 85, measurement image is captured by the image capture element 22.

For example, in the measurement of the objective eye refractive power, preliminary measurement of an eye refractive power is first performed, and the display 31 is moved in a direction of the optical axis L2 based on a result of the preliminary measurement, and thus fogging may be applied to the examinee's eye E. In other words, the display 31 may be moved once to a position where the examinee's eye E is brought into focus. Thereafter, the measurement of the eye refractive power may be performed with respect to the examinee's eye to which the fogging is applied. In the measurement, the measurement image is captured by the image capture element 22, and an output signal from the image capture element 22 is stored as image data (measurement image) in the memory 72. Thereafter, the control section 70 analyzes a ring image stored in the memory 72 to obtain the value of a refractive power in each longitudinal direction. The control section 70 performs predetermined processing with respect to the refractive power to obtain objective eye refractive powers (objective values) of S (spherical power), C (astigmatic power), and A (astigmatic axis angle) of the eye of the examinee in a case of the far sight. The obtained objective values in a case of the far sight are stored in the memory 72.

In the above-described measurement of the objective eye refractive power, the control section 70 may control the correction optical system 90 and may correct optical aberration occurring in the optical path of the objective measurement optical system 10. In this case, the amount of correction that corresponds to the refraction power measured by the objective measurement optical system 10 is acquired from the memory 72, and the correction optical system 90 is controlled based on the acquired amount of aberration correction.

More specifically, the amount of correction is set in accordance with the eye refractive power obtained through the preliminary measurement, and the correction optical system 90 is driven based on the set amount of correction. Thereby, the measurement is performed in a state where aberration occurring in the optical path of the objective measurement optical system 10 is corrected, and thus it is possible to measure the objective eye refractive power with high accuracy. Meanwhile, in a case where the eye refractive power is consecutively measured (for example, the measurement is performed a plurality of times), the correction optical system 90 may be controlled based on each measurement result.

Meanwhile, in the above-described description, the objective eye refractive power has been measured through a far sight, but the invention is nut limited thereto, and art objective eye refractive power through a near sight which is an eye refractive power in a state where the visual target is presented at a near distance may be measured. In addition, the measurement of the objective eye refractive power may be executed for the left and right eyes at the same time, and may be individually performed for each of the left and right eyes.

<Subjective Measurement (S3)>

Subsequently, subjective measurement (S3) is performed. When the measurement of the objective refractive power is completed and the monitor (in the present example, also serves as an operation section) 4 is operated, switching to a subjective far sight measurement (subjective refractive power measurement) mode is performed. In the subjective measurement, the spherical power S, the astigmatic power C, and the astigmatic axis angle A may be obtained at the beginning.

For example, the control section 70 may control the display 31 to display a required visual acuity value visual target on the optical axis L2 (for example, a visual target having a visual acuity value of 0.8). When an initial presentation visual target is presented to the examinee's eye, the examiner performs far sight measurement of the examinee. When a predetermined switch of the monitor 4 is pressed, a visual acuity value visual target to be presented is switched.

In addition, for example, the control section 70 changes the distance in the X direction between the left eye optical path and the right eye optical path based on the pupillary distance of the examinee measured at the time of the objective measurement. For example, the control section 70 drives the right eye deflection mirror 81R and the left eye deflection mirror 81L based on the pupillary distance, and rotates the mirrors in the X directions.

For example, when the initial setting of the subjective measurement is completed, the subjective measurement can be started. For example, in the subjective measurement, the examiner performs switching to a visual target having a visual acuity value higher by one step in a case where the answer of the examinee is a correct answer. On the other hand, the examiner performs switching to a visual target having a visual acuity value lower by one step in a case where the answer of the examinee is a wrong answer. In other words, the control section may switch a visual target based on a signal for changing a visual acuity value from the monitor 4.

In addition, the examiner may change a calibration power of the calibration optical system 60 by using the monitor 4 to obtain a far measurement subjective value (a spherical power S, an astigmatic power C, and an astigmatic axis angle A) of the examinee's eye.

Meanwhile, the calibration power of the calibration optical system 60 may be set to be a calibration power for each of the left and right eyes, or may be set to be the same calibration power for the left and right eyes. In addition, the measurement of the subjective eye refractive power may be performed for the left and right eyes at the same time, and may be individually performed for each of the left and right eyes. In addition, in a case of different timings, the visual target may not be displayed on the display 31 of the non-measurement, eyes, or fogging (for example, a constant refraction power is added to the objective value) may be performed by the calibration optical system 60.

For example, when the examination of the far measurement subjective value (spherical power S, astigmatic power C, and astigmatic axis angle A) of the examinee's eye is completed, the examiner stores the measurement result (examination result) in the memory 72 using the switch of the controller 3, and shifts to the binocular visual function examination which is the next examination. In addition, in the present example, oblique position examination is performed as one of the binocular visual function examinations.

Figure 7A:
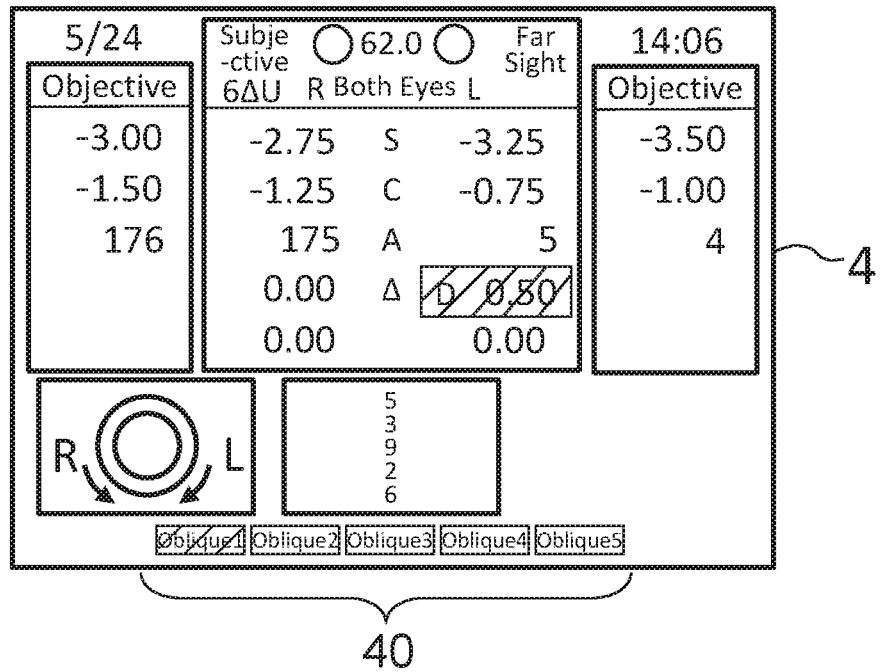
FIGS. 7A and 7B illustrate display screens of a monitor 4 in oblique position examination.
Figure 7B:
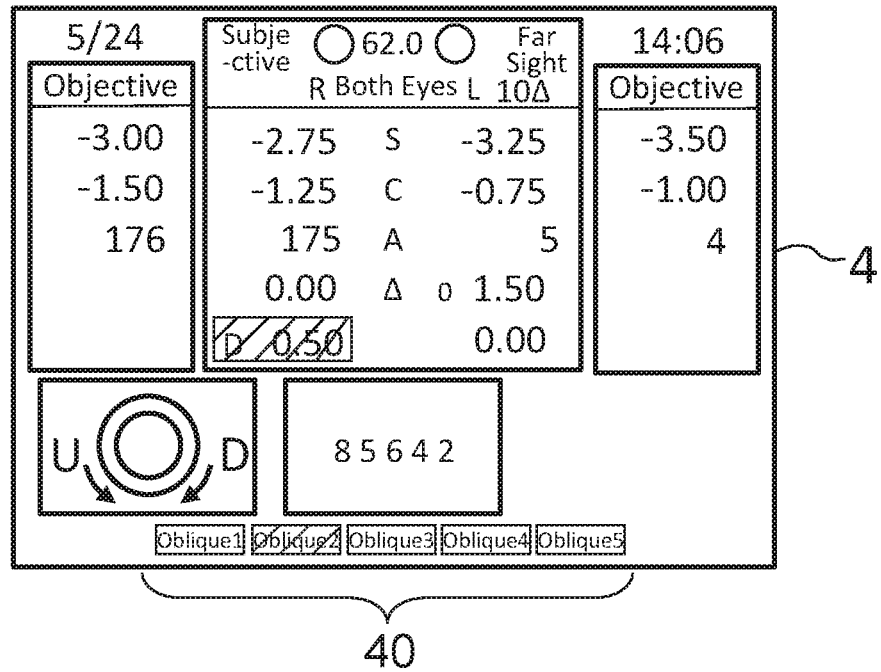
Figure 8A:
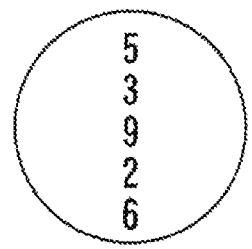
FIGS. 8A to 8C illustrate visual targets in horizontal oblique position examination.
Figure 8B:
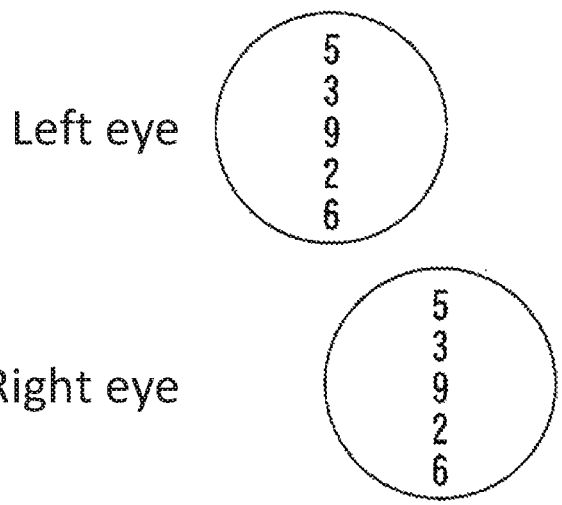
Figure 8C:
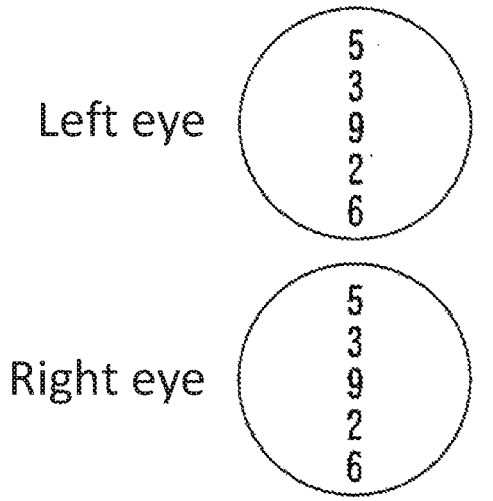

For example, FIGS. 7A and 7B illustrate display screens of the monitor 4 in the oblique position examination. For example, FIGS. 8A to 8C illustrate visual targets in the horizontal oblique position examination. FIGS. 9A and 9B are views for describing the application of the prism using the deflection mirrors 81. For example, as illustrated in FIG. 7A, the control section 70 causes a selection item 40 of the monitor 4 to display an oblique position 1 to an oblique position 5. For example, at the oblique position 1 to the oblique position 5 of the selection item 40, the items of the oblique position examination are prepared. For example, when the examiner presses the oblique position 1 of the selection item 40, the control section 70 reverses and displays the display of the oblique position 1 of the selection item 40 and presents the longitudinal single-row visual target to the examinee's eye.

For example, the control section 70 rotates the right eye deflection mirror 81R in the downward direction (the direction in which the mirror surface of the deflection mirror 81R moves downward). For example, the control section 70 rotates the deflection mirror 81R in the downward direction such that the prism power applied to the right eye as A and the base direction as B. U. (upper part of the base) for example, the control section 70 can apply 6 Δ B. U. to the right eye by rotating the right eye deflection mirror 81R in the downward direction.

In addition, for example, the control section 70 projects a longitudinal single-row of examination visual targets as illustrated in FIG. 8A consisting of the smallest characters that can be correctly read by the examinee or slightly larger characters, to the screen, and presents the examination visual target to the examinee's eye.

For example, the examiner confirms that the visual target is divided into two upper and lower parts with respect to the examinee. In addition, when the left eye of the examinee is shielded and the shield is removed, it is confirmed whether or not the visual target is deviated in the horizontal direction. For example, a case where the lower visual target (the visual target being viewed with the right eye) appears to be shifted to the right side as illustrated in FIG. 8B, indicates an inner oblique position.

For example, the examiner operates a switch (not illustrated) displayed on the monitor 4 to apply the prism. For example, in a case of the inner oblique position, the examiner operates a switch (not illustrated) displayed on the monitor 4, a B. O. (outer part of the base) prism is added and corrected. For example, when the examiner performs an operation for adding the B. O. prism, the control section 70 rotates the right eye deflection rumor 81R in the left direction (the direction in which the mirror surface of the deflection mirror 81R faces left) (refer to FIGS. 9A and 9B). For example, by rotating the right eye deflection mirror 81R in the left direction from the state of FIG. 9A to the state of FIG. 9B, the B. O. prism can be applied to the examinee's eye. For example, by rotating the right eye deflection mirror SIR in the left direction, the prism power applied to the examinee's eye is changed. For example, the B. O. prism is added and corrected, and as illustrated in FIG. 8C, the right eye deflection mirror 81R is rotated in the left direction until the upper and lower visual targets are at the same position (until there is no deviation).

In addition, in the present example, in a case of the inner oblique position, by rotating the right eye deflection mirror 81R in the left direction, a configuration in which the B. O. prism is applied to the examinee's eye has been described as an example, but the invention is not limited thereto. For example, a configuration may be adopted in which the B. O. prism is applied to the examinee's eye by rotating the left eye deflection mirror 81L in the right direction. Further, for example, a configuration may be adopted in which the B. O.

prism is applied to the examinee's eye by rotating the right eye deflection mirror 81R in the left direction and by rotating the left eye deflection mirror 81L in the right direction.

In addition, for example, when the left eye of the examinee is shielded and the shield is removed, it is confirmed whether or not the visual target is deviated in the horizontal direction, and a case where the visual target (the visual target being viewed with the right eye) appears to be shifted on the left side is an outer oblique position. For example, the examiner operates a switch (not illustrated) displayed on the monitor 4 to apply the prism. For example, in a case of the outer oblique position, the examiner operates a switch (not illustrated) displayed on the monitor 4, a B. I. (inner part of the base) prism is added and corrected. For example, when the examiner performs an operation for adding the B. I. prism, the control section 70 rotates the right eye deflection mirror 81R in the right direction (the direction in which the mirror surface of the deflection mirror 81R faces right). For example, a configuration may be adopted in which the B. O. prism is applied to the examinee's eye by locating the right eye deflection mirror 81R in the right direction. For example, by rotating the right eye deflection mirror 81R in the right direction, the prism power applied to the examinee's eye is changed. For example, the B. I. prism is added and corrected, and as illustrated in FIG. 8C, the right eye deflection mirror 81R is rotated in the right direction until the upper and lower visual targets are at the same position (until there is no deviation).

In addition, in the present example, in a case of the outer oblique position, by rotating the right eye deflection mirror 81R in the right direction, a configuration in which the B. I. prism is applied to the examinee's eye has been described as an example, but the invention is not limited thereto. For example, a configuration may be adopted in which the B. I, prism is applied to the examinee's eye by rotating the left eye deflection rumor 81L in the left direction. Further, for example, a configuration may be adopted in which the B. I. prism is applied to the examinee's eye by rotating the right eye deflection mirror 81R in the right direction and by rotating the left eye deflection mirror 81L in the left direction.

As described above, for example, when it is possible to confirm from the examinee that the deviation of the upper and lower visual targets disappears, the oblique position 2 (refer to FIGS. 7A and 7B) of the selection item 40 is pushed and the process proceeds to the next examination item. For example, when the examination item different from the current examination item is selected, the control section 70 stores the measurement value (for example, prism power and base direction) obtained by the current examination item in the memory 72.

Figure 10A:
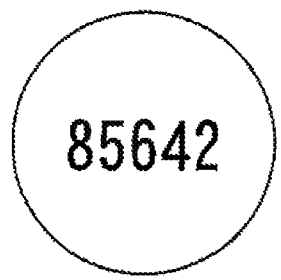
FIGS. 10A to 10C illustrate visual targets in vertical oblique position examination.
Figure 10B:
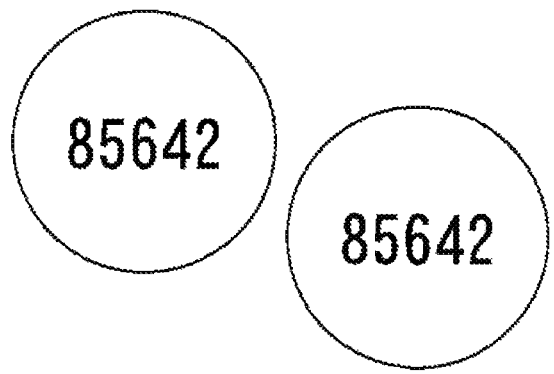
Figure 10C:
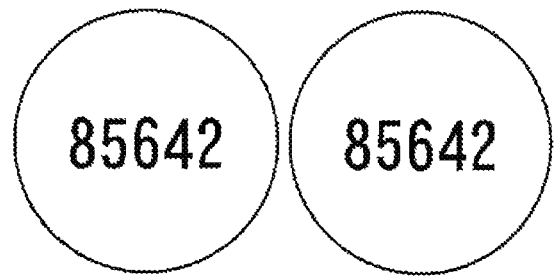

For example, FIGS. 10A to 10C illustrate the visual targets in the vertical oblique position examination. For example, when the oblique position 2 of the selection item 40 is pressed, as illustrated in FIG. 7B, the control section 70 reverses and displays the display of the oblique position 2 of the selection item 40 and presents the longitudinal single-row visual target to the examinee's eye.

For example, the control section 70 rotates the left eye deflection mirror 81L in the left direction (the direction in which the mirror surface of the deflection mirror 81L moves leftward). For example, the control section 70 rotates the deflection mirror 81L in the left direction such that the prism power applied to the left eye as 10 Δ and the base direction as B. I. (inner part of the base). For example, the control section 70 can apply 10 Δ B. I. to the left eye by rotating the left eye deflection mirror 81L in the left direction.

In addition, for example, the control section 70 projects a longitudinal single-row of examination visual targets as illustrated in FIG. 10A consisting of the smallest characters that can be correctly read by the examinee or slightly larger characters, to the screen, and presents the examination visual target to the examinee's eye.

For example, the examiner confirms that the visual target is divided into two left and right parts with respect to the examinee. In addition, when the left eye of the examinee is shielded and the shield is removed, it is confirmed whether or not the visual target is deviated in the up-down direction. For example, a case where the left visual target (the visual target being viewed with the left eye) appears to be shifted to the upper side as illustrated in FIG. 10B, indicates a right eye upper oblique position.

For example, the examiner operates a switch (not illustrated) displayed on the monitor 4 to apply the prism. For example, in a case of the right eye upper oblique position, the examiner operates a switch (not illustrated) displayed on the monitor 4, a B. D. (lower part of the base) prism is added and corrected. For example, when the examiner performs an operation for adding the B. D. prism, the control section 70 rotates the left eye deflection mirror 81L in the downward direction (the direction in which the mirror surface of the deflection mirror 81L faces down). For example, a configuration may be adopted in which the B. D. prism is applied to the examinee's eye by rotating the left eye deflection mirror 81L in the downward direction. For example, by rotating the left eye deflection mirror 81L in the downward direction, the prism power applied to the examinee's eye is changed. For example, the B. D. prism is added and corrected, and as illustrated in FIG. 10C, the left eye deflection mirror 81L is rotated in the downward direction until the left and right visual targets are at the same position (until there is no deviation).

In addition, in the present example, in a case of the right eye upper oblique position, by rotating the left eye deflection mirror 81L in the downward direction, a configuration in which the B. D. prism is applied to the examinee's eye has been described as an example, but the invention is not limited thereto. For example, a confirmation may be adopted us which the B. D, prism is applied to the examinee's eye by rotating the right eye deflection mirror 81R in the upward direction. Further, for example, a configuration may be adopted in which the B. D. prism is applied to the examinee's eye by rotating the left eye deflection mirror 81L in the downward direction and by rotating the right eye deflection mirror 81R in the upward direction.

In addition, for example, when the left eye of the examinee is shielded and the shielding is removed, it is confirmed whether or not the visual target is deviated in the horizontal direction, and a case where the right, visual target (the visual target being viewed with the right eye) appears to be shifted to the upper side indicates a left eye upper oblique position.

For example, the examiner operates a switch (not illustrated) displayed on the monitor 4 to apply the prism. For example, in a case of the left eye upper oblique position, the examiner operates a switch (not illustrated t displayed on the monitor 4, a B. U. (upper part of the base) prism is added and corrected. For example, when the examiner performs an operation for adding the B. U. prism, the control section 70 rotates the left eye deflection mirror 81L in the upward direction (the direction in which the mirror surface of the deflection mirror 81L faces up) For example, a configuration may be adopted in which the B. U. prism is applied to the examinee's eye by rotating the left eye deflection mirror 81L in the downward direction. For example, by rotating the left eye deflection mirror 81L in the upward direction, the prism power applied to the examinee's eye is changed. For example, the B. U. prism is added and corrected, and as illustrated in FIG. 10C, the left eye deflection mirror 81L is rotated in the upward direction until the left and right visual targets are at the same position (until there is no deviation).

In addition, in the present example, in a case of the left eye upper oblique position, by rotating the left eye deflection mirror 81L in the upward direction, a configuration in which the B. U. prism is applied to the examinee's eye has been described as an example, but the invention is not limited thereto. For example, a configuration may be adopted in which the B. U. prism is applied to the examinee's eye by rotating the right eye deflection mirror 81R in the downward direction. Further, for example, a configuration may be adopted in which the B. U. prism is applied to the examinee's eye by rotating the left eye deflection mirror 81L in the upward direction and by rotating the right eye deflection mirror 81R in the downward direction.

As described above, for example, when it is confirmed from the examinee that the deviation of the left and right visual targets disappears, the oblique position examination is completed by selecting an oblique position examination completion switch (not illustrated). For example, when the oblique position examination completion switch (not illustrated) is selected, the control section 70 stores the measurement value (for example, prism power and base direction) obtained by the current examination item in the memory 72. Further, for example, the control section 70 calculates the correction prism value in the horizontal direction and the correction prism value in the up-down direction from the measurement result of the oblique position examination stored in the memory 72, stores the prism value calculated as the final measurement result of the oblique position examination in the memory 72, and displays the prism values of the horizontal oblique position examination and the up-down oblique position examination on the monitor 4. In this manner, the prism value of the examinee's eye can be calculated.

In addition, after the far subjective measurement is completed, switching to a subjective near sight measurement node may be performed. When the near sight measurement mode is set, the control section 70 may control the light projecting optical system 30, may change a convergence angle by the deflection mirrors 81, and may present the visual target at a near position. In other words, the control section 70 may change the convergence amount (convergence angle) of the light projecting optical system 70 by rotating the deflection mirrors 81. Meanwhile, the presenting distance of the visual target in near examination may be changed in any manner based on an operation signal received from the operation section 4. As a result, the presenting distance of the usual target is changed from the far position to the near position. Meanwhile, in the near examination, the presenting distance of the visual target may be changed at the neat position to subjectively obtain an addition and an adjusting power. Further, the control section 70 may control the light deflection member in accordance with the change in presentation position of the visual target, and may change the convergence angles of left and right target light fluxes.

Furthermore, the control section 70 may change the distance in the X direction between the left eye optical path and the right eye optical path in accordance with the change in presentation position of the visual target. In other words, the pupillary distance may be changed to the pupillary distance for the near sight. In addition, for example, the control section 70 may drive the right eye deflection mirror 81R and the left eye deflection mirror 81L based on the pupillary distance for the near sight, and may rotate the mirrors in the X direction.

In addition, similar to the far examination, in the near examination, for example, the examiner may change the calibration power of the calibration optical system 60 by using a predetermined switch of the monitor 4, and may measure the near subjective value (spherical power S, astigmatic power C, and astigmatic axis angle A) in a state where the near visual target is presented. In addition, in the near examination, the control section 70 may change the amount of aberration correction of the correction optical system 90 in accordance with the change in calibration power.

For example, when the examination of the far measurement subjective value (spherical power S, astigmatic power C, and astigmatic axis angle A) of the examinee's eye is completed, the examiner may store the measurement result (examination result) in the memory 72 using the switch of the controller 3, and may shift to the binocular visual function examination (for example, the oblique position examination) for the neat sight which is the next examination.

Above, for example, the subjective optometry apparatus may include the light projecting optical system which includes the right eye light projecting optical system and the left eye light projecting optical system which are provided in a left and right pan, and projects the target light flux toward the examinee's eye to project the visual target onto the examinee's eye, the calibration optical system which includes the right calibration optical system and the left eye calibration optical system which are provided in a left and right pair, is disposed in the optical path from the light projecting optical system to the examinee's eye, and changes the optical characteristics of the target light flux, and the optical member which guides the target light flux of which the optical characteristics is changed by the calibration optical system to the examinee's eye, and the subjective optometry apparatus may subjectively measure the optical characteristics of the examinee's eye. In addition, for example, the subjective optometry apparatus may include: the light deflection section which is a member different from the calibration optical system, includes the light deflection members provided in a left and right pair respectively and the driving section configured to rotationally drive the light deflection members, and deflects the target light flux by rotating the light deflection members, the setting section which sets prism information related to deflection of line of sight of the examinee, and the control section which controls the light deflection section based on the prism information set by the setting section to deflect the target light flux. With such a configuration, complicated control is not required and it is possible to easily examine a visual function with a simple configuration.

In addition, for example, each of the light deflection members may be disposed at the position conjugated with the pupil of the examinee's eye in the light projecting optical system. According to this, it is possible to examine the visual function, for example, without increasing a driving range of the light deflection member. In other words, the light deflection section can be made smaller, and the size of the apparatus can be reduced.

In addition, for example, the light deflection section may deflect the target light flux in two dimensions. With such a configuration, the light deflection section can deflect the projection position of the target light flux with respect to the examinee's eye in various directions, such as the up-down and left-right directions. Therefore, it is possible to easily examine mote visual functions with a simple configuration.

In addition, for example, in the subjective optometry apparatus, a deviation detection section which detects a deviation of the target light flux with respect to the examinee's eye, may further be provided, the control section may control the light deflection section based on a detection result detected by the deviation detection section to deflect the target light flux. According to this, in a case of examining the visual function by changing the prism applied to the examinee's eye, it is possible to easily examine the visual function with a simpler configuration without providing an optical member dedicated to the calibration optical system. Further, for example, it is possible to perform a visual function examination and a deviation correction performed with the applied prism with a simpler configuration. Further, for example, it is possible to apply the prism, to perform the deviation correction, and to smoothly examine the visual function.

In addition, for example, in the subjective optometry apparatus, a pupillary distance setting section which sets a pupillary distance, may farther be provided, the control section may control the light deflection section based on the pupillary distance to deflect the target light flux. According to this, in a case of examining the visual function by changing the prism applied to the examinee's eye, it is possible to easily examine the visual function with a simpler configuration without providing an optical member dedicated to the calibration optical system. Further, for example, it is possible to perform the visual function examination and the adjustment of the pupillary distance which are performed with the applied prism with a simpler configuration. Further, for example, it is possible to apply the prism, to perform the adjustment of the pupillary distance, and to smoothly examine the visual function.

In addition, for example, in the subjective optometry apparatus, a convergence amount setting section which sets a convergence amount (convergence angle) of the light projecting optical system may further be provided, the control section may control the light deflection section based on the convergence amount to defied the target light flux. According to this, in a case of examining the visual function by changing the prism applied to the examinee's eye, it is possible to easily examine the visual function with a simpler configuration without providing an optical member dedicated to the calibration optical system. Further, for example, it is possible to perform the visual function examination and the adjustment of the convergence amount of the light projecting optical system which are performed with the applied prism with a simpler configuration. In addition, for example, it is possible to apply the prism, to perform the adjustment of the convergence amount, and to smoothly examine the visual function.

In addition, in the oblique position examination, the examination is not limited to the oblique position examination. The technology of the present disclosure can be applied in various oblique position examination. For example, various types of oblique position examination may include oblique position examination in which the cross eye visual target is presented to the examinee's eye, oblique position examination using a cross view with a fixation point, oblique position examination using a cross ring visual target, and the like. In addition for example, as various oblique position examination, a cover uncover test may be used. In this case, for example, it may be determined whether or not there is the oblique position by capturing the anterior ocular segment image, and an oblique position amount and a restored position amount may be acquired.

What is claimed is:

1. A subjective optometry apparatus that subjectively measures optical characteristics of an examinee's eye, comprising:

a light projecting optical system that includes a right eye light projecting optical system and a left eye light projecting optical system which are provided in a left and right pair, and projects a target light flux toward the examinee's eye to project a visual target onto the examinee's eye;

a calibration optical system that includes a right eye calibration optical system and a left eye calibration optical system which are provided in a left and right pair, is disposed in an optical path from the light projecting optical system to the examinee's eye, and changes optical characteristics of the target light flux;

an optical member that guides the target light flux of which the optical characteristics is changed by the calibration optical system to the examinee's eye;

a light deflection section that is a member different from the calibration optical system, includes light deflection members provided in a left, and right pair respectively and a driving section configured to rotationally drive the light deflection members, and deflects the target light flux by rotating the light deflection members;

a setting section that sets prism information; and a control section that controls the light deflection section based on the prism information set by the setting section to deflect the target light flux;

wherein each of the light deflection members is disposed at a position conjugated with a pupil of the examinee's eye in the light projecting optical system.

2. The subjective optometry apparatus according to claim 1, wherein the light deflection section deflects the target light flux in two dimensions.

3. The subjective optometry apparatus according to claim 1, further comprising:

a deviation detection section that detects a deviation of the target light flux with respect to the examinee's eye, wherein the control section controls the light deflection section based on a detection result detected by the deviation detection section to deflect the target light flux.

4. The subjective optometry apparatus according to claim 1, further comprising:

a pupillary distance setting section that sets a pupillary distance, wherein the control section controls the light deflection section based on the pupillary distance to deflect the target light flux.

5. The subjective optometry apparatus according to claim 1, further comprising:

a convergence amount setting section that sets a convergence amount of the light projecting optical system, wherein the control section controls the light deflection section based on the convergence amount to deflect the target light flux.

6. The subjective optometry apparatus according to claim 1, wherein the light projecting optical system includes a light source configured to project the target light flux toward the examinee's eye, and the light deflection members are disposed in an optical path between the optical member and the light source.

7. A subjective optometry apparatus that subjectively measures optical characteristics of an examinee's eye, comprising:
- a light projecting optical system that includes a right eye light projecting optical system and a left eye light projecting optical system which are provided in a left and right pair, and emits a target light flux toward the examinee's eye by displaying a visual target on a display to project the visual target onto the examinee's eye;
- a calibration optical system that includes a right eye calibration optical system and a left eye calibration optical system which are provided in a left and right pair, is disposed in an optical path from the light projecting optical system to the examinee's eye, and changes optical characteristics of the target light flux;
- an optical member that guides the target light flux of which the optical characteristics is changed by the calibration optical system to the examinee's eye;
- a light deflection section that is a member different from the calibration optical system, includes light deflection members provided in a left and right pair respectively and a driving section configured to rotationally drive the light deflection members, and deflects the target light flux by rotating the light deflection members;
- a setting section that sets prism information; and
- a control section that changes a position of the visual target displayed on the display based on the prism information set by the setting section,
- wherein each of the light deflection members is disposed at a position conjugated with a pupil of the examinee's eye in the light projecting optical system.

8. A subjective optometry apparatus that subjectively measures optical characteristics of an examinee's eye, comprising:
- a light projecting optical system that includes a right eye light projecting optical system and a left eye light projecting optical system which are provided in a left and right pair, and projects a target light flux toward the examinee's eye to project a visual target onto the examinee's eye;
- a calibration optical system that includes a right eye calibration optical system and a left eye calibration optical system which are provided in a left and right pair, is disposed in an optical path from the light projecting optical system to the examinee's eye, and changes optical characteristics of the target light flux;
- an optical member that guides the target light flux of which the optical characteristics is changed by the calibration optical system to the examinee's eye;
- a light deflection section that is a member different from the calibration optical system, includes light deflection members provided in a left, and right pair respectively and a driving section configured to rotationally drive the light deflection members, and deflects the target light flux by rotating the light deflection members;
- one or more processors configured to set prism information and control the light deflection section based on the set prism information to deflect the target light flux;
- wherein each of the light deflection members is disposed at a position conjugated with a pupil of the examinee's eye in the light projecting optical system.

9. The subjective optometry apparatus according to claim 1, wherein the light deflection section deflects the target light flux in two dimensions.

10. The subjective optometry apparatus according to claim 1, further comprising:
- an alignment index light projecting optical system that detects a deviation of the target light flux with respect to the examinee's eye,
- wherein the one or more processors controls the light deflection section based on a detected deviation of the target light flux with respect to the examinee's eye to deflect the target light flux.

11. The subjective optometry apparatus according to claim 1, wherein the one or more processors set a pupillary distance,
- wherein the one or more processors controls the light deflection section based on the pupillary distance to deflect the target light flux.

12. The subjective optometry apparatus according to claim 1, wherein the one or more processors set a convergence amount of the light projecting optical system,
- wherein the one or more processors controls the light deflection section based on the convergence amount to deflect the target light flux.

13. The subjective optometry apparatus according to claim 1,
- wherein the light projecting optical system includes a light source configured to project the target light flux toward the examinee's eye, and
- the light deflection members are disposed in an optical path between the optical member and the light source.

14. A subjective optometry apparatus that subjectively measures optical characteristics of an examinee's eye, comprising:
- a light projecting optical system that includes a right eye light projecting optical system and a left eye light projecting optical system which are provided in a left and right pair, and emits a target light flux toward the examinee's eye by displaying a visual target on a display to project the visual target onto the examinee's eye;
- a calibration optical system that includes a right eye calibration optical system and a left eye calibration optical system which are provided in a left and right pair, is disposed in an optical path from the light projecting optical system to the examinee's eye, and changes optical characteristics of the target light flux;
- an optical member that guides the target light flux of which the optical characteristics is changed by the calibration optical system to the examinee's eye;
- a light deflection section that is a member different from the calibration optical system, includes light deflection members provided in a left and right pair respectively and a driving section configured to rotationally drive the light deflection members, and deflects the target light flux by rotating the light deflection members; and
- one or more processors configured to set prism information and change a position of the visual target displayed on the display based on the prism information,
- wherein each of the light deflection members is disposed at a position conjugated with a pupil of the examinee's eye in the light projecting optical system.

* * * * *